United States Patent
Cuero Rengifo et al.

(10) Patent No.: US 9,868,811 B2
(45) Date of Patent: Jan. 16, 2018

(54) POLYURETHANE BIOFOAMS DERIVED FROM NATURAL PRODUCTS AND METHODS OF MAKING AND USING THEREOF

(71) Applicants: INTERNATIONAL PARK OF CREATIVITY, Bogota (CO); Raul Cuero Rengifo, Cypress, TX (US); Gabriela Melo Rodriguez, Bogota (CO)

(72) Inventors: Raul Cuero Rengifo, Cypress, TX (US); Gabriela Melo Rodriguez, Bogota (CO)

(73) Assignee: INTERNATIONAL PARK OF CREATIVITY, Bogota (CO)

( * ) Notice: Subject to any disclaimer, the term of this patent is extended or adjusted under 35 U.S.C. 154(b) by 0 days.

(21) Appl. No.: 14/909,170

(22) PCT Filed: Aug. 4, 2014

(86) PCT No.: PCT/US2014/049530
§ 371 (c)(1),
(2) Date: Feb. 1, 2016

(87) PCT Pub. No.: WO2015/017847
PCT Pub. Date: Feb. 5, 2015

(65) Prior Publication Data
US 2016/0168311 A1 Jun. 16, 2016

Related U.S. Application Data

(60) Provisional application No. 61/861,446, filed on Aug. 2, 2013.

(51) Int. Cl.
| | | |
|---|---|---|
| *C08G 18/64* | (2006.01) |
| *C08G 18/08* | (2006.01) |
| *C08G 18/34* | (2006.01) |
| *C08G 18/24* | (2006.01) |
| *C08G 18/18* | (2006.01) |
| *C08G 18/16* | (2006.01) |
| *C08G 18/36* | (2006.01) |
| *C08G 18/76* | (2006.01) |
| *C08K 3/22* | (2006.01) |
| *C08K 3/36* | (2006.01) |
| *C08K 3/34* | (2006.01) |
| *A61K 35/56* | (2015.01) |
| *C08L 75/04* | (2006.01) |
| *C08G 101/00* | (2006.01) |
| *A61K 35/63* | (2015.01) |

(52) U.S. Cl.
CPC ......... *C08G 18/6484* (2013.01); *C08G 18/14* (2013.01); *C08G 18/165* (2013.01); *C08G 18/1825* (2013.01); *C08G 18/246* (2013.01); *C08G 18/348* (2013.01); *C08G 18/36* (2013.01); *C08G 18/7621* (2013.01); *C08G 18/7671* (2013.01); *C08K 3/22* (2013.01); *C08K 3/34* (2013.01); *C08K 3/36* (2013.01); *A61K 35/63* (2015.01); *C08G 2101/0008* (2013.01); *C08G 2101/0083* (2013.01)

(58) Field of Classification Search
CPC .... C08G 2101/0008; C08G 2101/0083; C08G 18/6484; C08G 18/14; C08G 18/348; C08G 18/7671; C08G 18/165; C08G 18/246; C08G 18/1825; C08G 18/7621; C08G 18/36; A61K 35/63; C08L 75/04; C08K 3/22; C08K 3/34; C08K 3/36
See application file for complete search history.

(56) References Cited

U.S. PATENT DOCUMENTS

| | | | |
|---|---|---|---|
| 5,821,271 A | 10/1998 | Roenigk | |
| 2002/0019450 A1* | 2/2002 | Fukuzawa | A45D 33/34 521/82 |
| 2004/0170670 A1 | 9/2004 | Smith et al. | |
| 2009/0054542 A1* | 2/2009 | Schoenberger | A61L 15/26 521/137 |
| 2009/0068250 A1* | 3/2009 | Gravagna | A61L 27/24 424/426 |
| 2009/0238811 A1 | 9/2009 | McDaniel et al. | |
| 2013/0022643 A1 | 1/2013 | Sternoff et al. | |

FOREIGN PATENT DOCUMENTS

WO 2012027111 3/2012

OTHER PUBLICATIONS

International Search Report and Written Opinion for PCT/US14/49530 dated Nov. 7, 2014.

* cited by examiner

*Primary Examiner* — Rabon Sergent
(74) *Attorney, Agent, or Firm* — Gardner Groff Greenwald & Villanueva, PC

(57) ABSTRACT

Described herein are polyurethane compositions based on natural materials, as well as methods for making and using the compositions. Also described herein are biofoams made from the polyurethane compositions. The biofoams described herein are resistant to degradation by acid and heat and are able to recover their original shapes after the application of pressure.

19 Claims, 17 Drawing Sheets

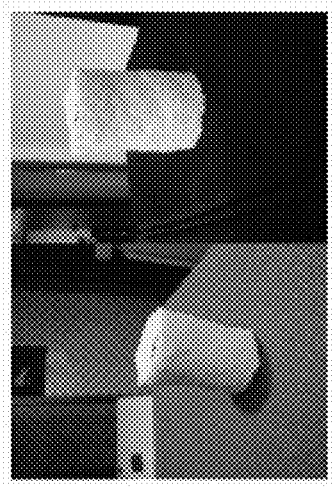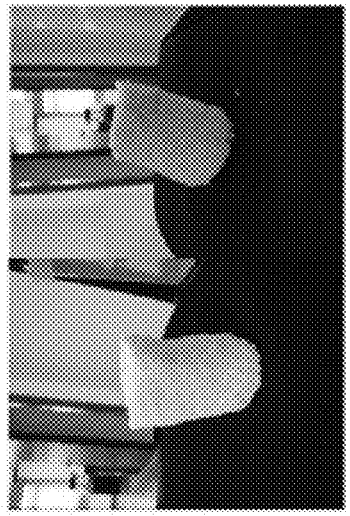
FIGURE 23
FIGURE 24

POLYURETHANE BIOFOAMS DERIVED FROM NATURAL PRODUCTS AND METHODS OF MAKING AND USING THEREOF

CROSS REFERENCE TO RELATED APPLICATION

This application claims priority upon U.S. Provisional Application Ser. No. 61/861,446, filed Aug. 2, 2013. The application is hereby incorporated by reference in its entirety for all of its teachings.

BACKGROUND

Synthetic foams have been widely used as packing material; in mattresses and pet bedding; as cushioning in furniture, automobiles, and boats; in shoes and padded costumes; in the construction and building materials industries; and for a variety of biomedical applications. Polyurethanes are polymeric compositions that are commonly used in foam applications; polyurethanes are formed through the reaction of one or more polyfunctional alcohols with polyisocyanates. Foam formation occurs when a gas or low boiling point liquid is introduced to the reaction mixture during the polymerization process.

However, polyurethanes have many drawbacks. The raw materials for their synthesis are often hydrocarbon based and ultimately derived from petroleum, and synthesis is often carried out in organic solvents, which are expensive and difficult to dispose of, as well as potentially hazardous for the environment. Additionally, many polyurethanes are not biodegradable. Further, attempts to introduce natural polyols into polyurethane compositions have been limited, often due to the rarity and/or cost of the natural materials, or to their non-ideal physical and chemical characteristics. Finally, many polyurethane foams are not resistant to chemical exposure, such as exposure to acids, and many polyurethane foams are slow, or simply unable, to return to their original shapes and/or sizes after pressure has been applied.

It would thus be desirable to develop a polyurethane composition that is suitable for producing foams and that is based on inexpensive, readily-available natural products. Ideally, the synthesis of such a polyurethane would not require the use of organic solvents and the resulting foam would possess desirable properties such as acid resistance, heat resistance, and recovery of its original shape and size after the application of pressure.

SUMMARY

Described herein are polyurethane compositions derived from natural materials, as well as methods for making and using the compositions. Also described herein are biofoams made from the polyurethane compositions. The biofoams described herein are resistant to degradation by acid and heat and are able to recover their original shapes after the application of pressure. In one aspect, the polyurethanes are synthesized from acidic aqueous solutions of chitosan, castor oil, and 4,4'-methylene diphenyl diisocyanate.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 23 shows a biofoam of the present invention (a) before and (b) after one hour in an 80° C. oven.

FIG. 24 shows a biofoam of the present invention (a) before and (b) after one hour in a 120° C. oven.

DETAILED DESCRIPTION

Figure 1:
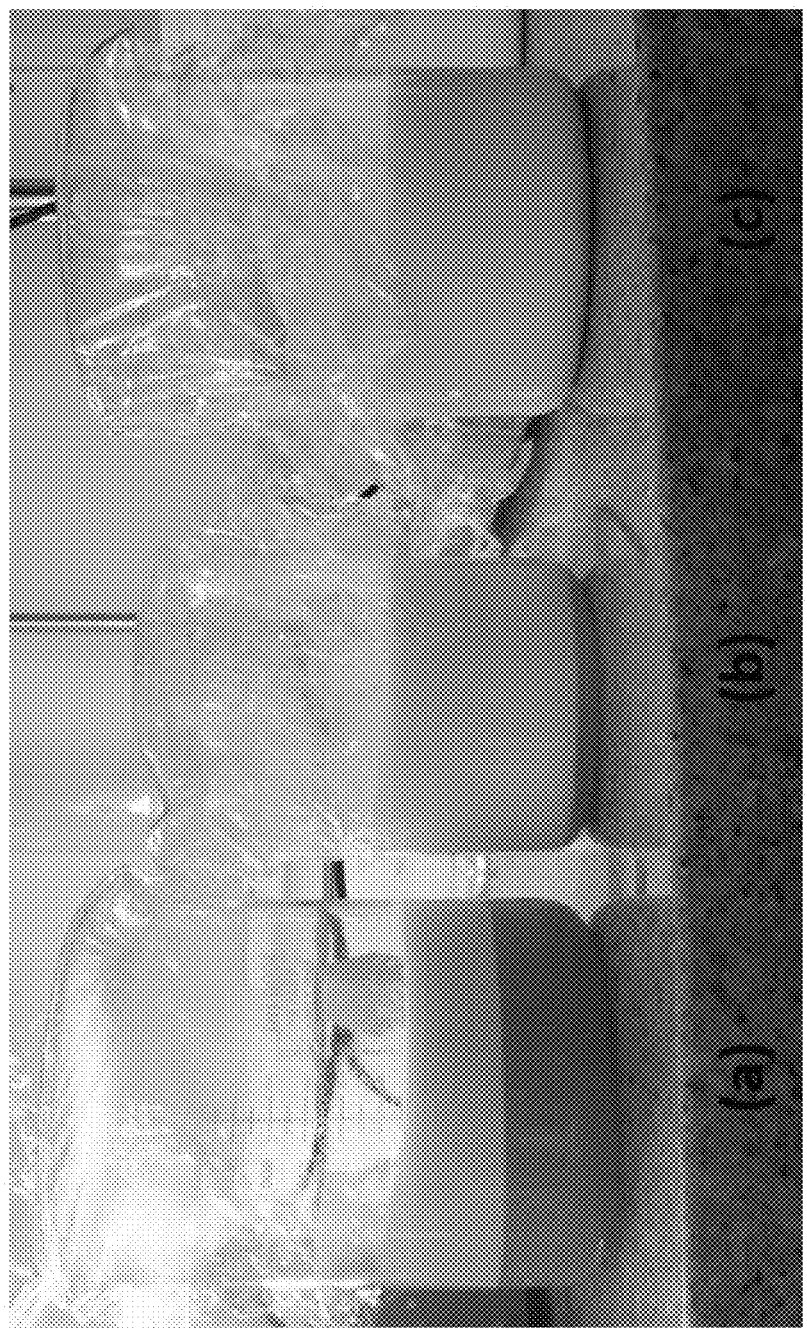
FIG. 1 shows mixtures of vegetable oils with 4% solutions of chitosan after 72 hours in the presence of various surfactants: (a) soy lecithin, (b) polysorbate 20, (c) polysorbate 80.

The compositions, methods, and articles described herein can be understood more readily by reference to the following detailed description. It is also to be understood that the terminology used herein is for the purpose of describing particular aspects only and is not intended to be limiting.

It must be noted that, as used in the specification and appended claims, the singular forms "a," "an," and "the" include plural referents unless the context clearly dictates otherwise. Thus, for example, reference to "a polysaccharide" includes mixtures of two or more polysaccharides.

"Optional" or "optionally" means that the subsequently described event or circumstance can or cannot occur, and that the description includes instances where the event or circumstance occurs and instances where it does not. For example, the phrase "a blowing agent is optionally applied" means that a blowing agent can or cannot be applied.

As used herein, the term "about" is used to provide flexibility to a numerical range endpoint by providing that a given value may be "a little above" or "a little below" the endpoint without affecting the desired result. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents. In one aspect, the admixture is an emulsion.

The term "alkyl" or "aliphatic" refers to, unless stated otherwise, straight or branched hydrocarbon radicals, such as methyl, ethyl, propyl, butyl, octyl, isopropyl, tert-butyl, sec-pentyl, and the like. Alkyl or aliphatic groups can either be unsubstituted or substituted with one or more substituents, e.g., halogen, alkoxy, aryl, arylalkyl, aralkoxy and the like. Alkyl or aliphatic groups include, for example, from 1 to 25 carbon atoms, from 1 to 8 carbon atoms, or from 1 to 4 carbon atoms.

The term "cycloalkyl group" or "cycloaliphatic group" as used herein is a non-aromatic carbon-based ring composed of at least three carbon atoms. Examples of cycloalkyl or cycloaliphatic groups include, but are not limited to, cyclopropyl, cyclobutyl, cyclopentyl, cyclohexyl, etc. The term "heterocycloalkyl group" or "heterocycloaliphatic group" is a cycloalkyl or cycloaliphatic group as defined above where at least one of the carbon atoms of the ring is substituted with a heteroatom such as, but not limited to, nitrogen, oxygen, sulfur, or phosphorus.

The term "aryl group" or "aromatic group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl or aromatic group can be substituted or unsubstituted. The aryl or aromatic group can be substituted with one or more groups including, but not limited to, alkyl, alkynyl, alkenyl, aryl, halide, nitro, amino, ester, ketone, aldehyde, hydroxy, carboxylic acid, or alkoxy.

"Cream time" as used herein is a property of a polyurethane foam and is defined as the time between the initial mixing of polyol and polyisocyanate and the appearance of foam expansion.

"Gel time" as used herein is a property of a polyurethane foam and is defined as the time between the initial mixing of polyol and polyisocyanate and the formation of a non-flowing, semi-solid system in the reaction vessel.

"Tack free time" as used herein is a property of a polyurethane foam and is defined as the time between the initial mixing of polyol and polyisocyanate and a level of curing such that the surface of the foam is no longer sticky.

"Drying" as used herein refers to the removal of residual water from a polyurethane biofoam.

"Discoloration" as used herein refers to a change in color of a foam upon exposure to a substance known to cause stains. In one aspect, the foams described herein are resistant to discoloration.

"Acid resistance" as used herein refers to the ability of the foams to maintain their shapes and physical characteristics and/or to resist decomposition upon exposure to acid. In one aspect, the foams described herein are acid resistant.

"Temperature resistance" as used herein refers the ability of the foams to maintain their shapes and physical characteristics upon exposure to temperature extremes. In one aspect, the foams described herein are temperature resistant.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference of each various individual and collective combination and permutation of these compounds may not be explicitly disclosed, each is specifically contemplated and described herein. For example, if a polyisocyanate is disclosed and discussed and a number of different natural oil polyols are discussed, each and every combination and permutation of diisocyanate and silicon polyol that is possible is specifically contemplated unless specifically indicated to the contrary. For example, if a class of molecules A, B, and C are disclosed, as well as a class of molecules D, E, and F, and an example of a combination molecule A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from the disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered from the disclosure of A, B, and C; D, E, and F; and the example combination A-D. This concept applies to all aspects of this disclosure including, but not limited to, steps in methods of making and using the disclosed compositions. Thus, if a variety of additional steps can be performed, it is understood that each of these additional steps can be performed with any specific embodiment or combination of embodiments of the disclosed methods, and that each such combination is specifically contemplated and should be considered disclosed.

Described herein are polyurethane compositions and biofoams derived therefrom. In one aspect, the polyurethane composition produced by the process comprising:
a. admixing a polysaccharide, a surfactant, and a natural oil polyol in a solvent to produce a first admixture; and
b. reacting the first admixture with a polyisocyanate to produce the polyurethane composition.

Each component used to prepare the polyurethane compositions as well as reaction conditions are discussed in detail below.

As used herein, a "polysaccharide" is a polymer composed of covalently-linked monosaccharides. The monosaccharides in the polysaccharide can be identical, or the polysaccharide can be composed of a mixture of monosaccharide units. The polysaccharide can be natural or synthetic, or can be a natural polysaccharide that has been chemically modified. "Polysaccharide" as used herein also includes mixtures of two or more polysaccharides. In one aspect, the polysaccharides useful herein include, for example, chitosan, chitin, cellulose, guar, or mixtures thereof. In another aspect, the polysaccharides useful herein include one or more glucosamine (GlcN) or N-acetylglucosamine (NAG) residues.

As used herein, "residue" is a monomer within a polymeric chain, such as a monosaccharide residue in a polysaccharide. Thus, for example, chitosan includes GlcN and NAG residues.

"Chitin" is a linear polymer of NAG residues. In some aspects, the chitin useful herein is extracted from the exoskeletons of insects, the cell walls of fungi, and/or the shells of crustaceans. In a further aspect, the crustaceans are crabs, lobsters, or shrimps.

"Chitosan" as used herein is a linear polymer of randomly-distributed GlcN and NAG residues. Chitosan may be obtained from chitin using alkali extraction or by any other technique known in the art. In one aspect, chitin is "deacetylated" using alkali to produce chitosan. In one aspect, deacetylation can remove some or all of the acetyl groups from the NAG residues of chitin. In one aspect, the chitin is from about 50% to about 100% acetylated. In a further aspect, the chitin is from about 50% to about 80% acetylated. In a still further aspect, the chitin is about 50% acetylated, about 60% acetylated, or about 77% acetylated. The molecular weight of the chitosan can vary. For example, the chitosan can contain about 3, 4, 5, 6, 7, 8, 9, 10, 11, 12, 13, 14, 15, 16, 17, 18, 19, 20, or any range thereof, of GlcN and/or NAG units. In another aspect, the chitosan can include 5 to 7 GlcN and/or NAG units.

"Guar," also known as "guar gum," is a carbohydrate obtained from the endosperm of the guar bean (*Cyamopsis tetragonoloba*). The primary polysaccharide in guar is called guaran and is made of a linear backbone of D-mannose monomers connected by β-(1→4) glycosidic bonds. To the mannose backbone are attached D-galactose monomers via α-(1→6) glycosidic bonds. In some aspects, the galactose residues are thought to follow a regular or repeating pattern of attachment to the mannose backbone. In other aspects, the galactose residues are believed to be randomly distributed, usually in groups of two or three. The ratio of mannose to galactose can be from about 1.6:1 to 2:1, or can be about 1.8:1. Guar is a naturally-occurring, high molecular weight, water-soluble polymer. In some aspects, the average molecular weight of guaran polymers is from about 220,000 to about 2,000,000 Da. In another aspect, the average molecular weight is from about 1,000,000 to about 2,000,000 Da.

"Cellulose" is a linear polysaccharide composed of β(1→4) linked D-glucose molecules that is the most abundant organic compound on earth, making up the primary cell walls of green plants and many types of algae. Cellulose is largely indigestible except by microorganisms such as, for example, by microorganisms in the guts of termites, cattle, and the like, as well as by some species of fungi. "Microcrystalline cellulose" as used herein is a form of cellulose that has been partially depolymerized through treatment of fibrous plant pulp with mineral acids. Microcrystalline cellulose has a low degree of polymerization and a small particle size; several different grades are commercially available.

Not wishing to be bound by theory, guar, cellulose, and like compounds interact with other polysaccharides such as, for example, chitosan, and increase the availability of hydroxyl groups in those polysaccharides for reactions with isocyanates. In one aspect, cellulose is added to the emulsion containing a polysaccharide, a surfactant, and a natural oil polyol at a concentration of 0.1%, 0.2%, 0.4%, 0.5%, 0.6%, 1%, 1.5%, 2%, 2.5%, 3%, 3.5%, 4%, or 5% (w/v) with respect to the emulsion volume. In another aspect, guar is added to the emulsion containing a polysaccharide, a surfactant, and a natural oil polyol at a concentration of 0.001%, 0.005%, 0.01%, 0.025%, 0.05%, 0.1%, 0.2%, 0.4%, 0.6%, 0.7%, or 1% (w/v) with respect to the emulsion volume.

In one aspect, the polysaccharide is incorporated into the polyurethane compositions described herein. In a further aspect, the polysaccharide is first dissolved in a solvent, then added to the reaction mixtures described herein. In one aspect, the solvent is water. In another aspect, the solvent is an aqueous solution of an acid. In a further aspect, the acid is acetic acid, hydrochloric acid, nitric acid, formic acid, or sulfuric acid. In one aspect, the concentration of acid can be 1%, 1.4%, 2%, 2.4%, 3%, 3.4%, 4%, 4.5% (v/v), or any range thereof (e.g., 1% to 4.5%, 2.4% to 4.5%, etc.). In yet another aspect, the acid can be present in the aqueous solution at a concentration of 0.01N to 1N, 0.05N to 0.5N, 0.05N to 0.15N, or about 0.1N. In a still further aspect, the solvent contains from about 0.01% to about 10% by weight of the polysaccharide, or about 0.01%, 0.02%, 0.05%, 0.1%, 0.5%, 1%, 1.5%, 2%, 2.5%, 3%, 3.5%, 4%, 4.5%, 5%, 5.5%, 6%, 7%, 8%, 9%, or 10% by weight of the polysaccharide. In one aspect, 4% (w/v) chitosan can be dissolved in 1.4% aqueous HCl. In one aspect, the solutions of polysaccharide are shaken at 200 rpm overnight to ensure adequate mixing.

A "polyol" as used herein is any organic molecule that contains one or more hydroxyl groups that are available to take part in organic reactions.

A "natural oil" as used herein is any oil extracted from a living organism. In one aspect, the living organism is a plant or alga. In a further aspect, the plant is the castor bean or castor oil plant (*Ricinus communis*). In another aspect, the living organism is an animal. In an alternative aspect, the living organism is a fungus. Natural oils can additionally contain triglycerides, fatty acids, fatty acid esters, sterols, isoprenoid or terpenoid compounds, alkaloids, phenols, and other metabolites.

"Natural oil polyols" are compounds derived from or present in natural oils that include at least one free hydroxyl group. A natural oil polyol may be naturally occurring, as with the ricinoleic acid in castor oil, or it may be chemically synthesized from an oil or fat containing one or more carbon-carbon double bonds. In one aspect, a natural fatty acid or triglyceride containing a carbon-carbon double bond is subjected to ozonolysis to cleave the double bond, followed by treatment with another molecule such as, for example, ethylene glycol, to form an alcohol. In another aspect, a natural fatty acid or triglyceride containing a carbon-carbon double bond can be epoxidized and treated with a nucleophile to generate an alcohol. In still another aspect, a natural fatty acid or triglyceride containing a carbon-carbon double bond can be formylated in the presence of carbon monoxide and hydrogen gas, followed by hydrogenation to generate a hydroxyl group. Other methods of producing natural oil polyols are also contemplated. Natural oils can be used as extracted or can optionally be purified. In one aspect, the natural oil polyol is or is derived from soy, a chemically-modified vegetable oil, a carbohydrate, lignin, cork, cashew nutshell liquid, *Lesquerella* oil, or a combination thereof. In one aspect, the natural oil polyol is castor oil. In another aspect, the natural oil polyol is ricinoleic acid. In still another aspect, the natural oil polyol is coriolic acid or a chemically-modified fatty acid.

"Castor oil" can optionally be extracted from the seeds of the castor oil plant. The primary component of castor oil is ricinoleic acid; minor components include oleic acid, linoleic acid, linolenic acid, stearic acid, palmitic acid, dihydroxystearic acid, and other trace fatty acids.

In one aspect, the natural polyol can include one or more hydroxy fatty acids, which is defined herein as a fatty acid having at least at least one free hydroxyl group. The hydroxy fatty acid has the general formula R'C(O)OH, wherein R' is a saturated or unsaturated hydrocarbon chain having from 10 to 25 carbon atoms, and at least one hydroxyl group is covalently attached to a carbon atom of the hydrocarbon chain. The hydrocarbon can be linear or branched. In the case when the hydrocarbon is unsaturated, the hydrocarbon can have one carbon-carbon double bond or multiple carbon-carbon double bonds. Examples of monohydroxy fatty acids (i.e., one hydroxyl group present on the fatty acid) include, but are not limited to, hydroxynervonic acid, cerebronic acid, 10-hydroxy-20 decenoic acid, hydrox-2-decenoic acid 10-phosphate, strophantus acid, lesquerolic acid, densipolic acid, auricolic acid, β-dimorphecolic acid, kamlolenic acid, 8-hydroxyoctadeca-9.11-diynoic acid, 8-hydroxyoctadeca-17-en-9.11-diynoic acid (Isanolic), or 8-hydroxyoctadeca-13.17-dien-9.11-diynoic acid. Examples of polyhydroxy fatty acids (i.e., two or more hydroxyl groups) include, but are not limited to, axillarenic acid, tetrapedic acids, byrsonic acid, 9,10-dihydroxyoctadecanoic acid, phaseolic acid, phloionolic acid, Resolvin D1, 10,17S-docosatriene, or Resolvin E1. The hydroxy fatty acids can be sued as is in the natural oil (e.g., castor oil), isolated from a natural oil, or synthesized accordingly.

A "surfactant" is an organic compound that may be derived from a natural product, or may result from chemical modification of a natural product, or may be completely chemically synthesized. Surfactants typically contain hydrophilic head groups and hydrophobic tails. In one aspect, the head group is anionic, cationic, nonionic, or zwitterionic. In another aspect, the tail is composed of a hydrocarbon or a glucoside. Surfactants alter the surface tension of liquids and may form micelles or bilayers in aqueous solution. Many applications of surfactants are known in the art. Surfactants are, for example, commonly employed as emulsifiers, detergents, wetting agents, and in other related uses.

Numerous cationic surfactants can be used in the compositions described herein. In one aspect, the cationic surfactant can be a quaternary ammonium salt.

Numerous zwitterionic surfactants can be used in the compositions described herein. In one aspect, the zwitterionic surfactant can be a lecithin such as soy lecithin; in another aspect, the zwitterionic surfactant can be a hydroxysultaine, a betaine, a sulfobetaine, or a mixture thereof. Among betaines, surfactants may be selected from the group comprising high alkyl betaines such as cetyl dimethyl carboxymethyl betaine, cocamidopropyl betaine, cocobetaine, coco dimethyl carboxymethyl betaine, lauryl amidopropyl betaine, lauryl bis-(2-hydroxyethyl) carboxymethyl betaine, lauryl bis-(2-hydroxypropyl)alpha-carboxyethyl betaine, lauryl dimethyl alphacarboxyethyl betaine, lauryl dimethyl carboxymethyl betaine, oleyl betaine, oleyl dimethyl gamma-carboxypropyl betaine, stearyl bis-(2-hydroxypropyl) carboxymethyl betaine, and mixtures thereof. Among sulfobetaines, surfactants may be selected from the group comprising coco dimethyl sulfopropyl betaine, lauryl bis-(2-hydroxyethyl) sulfopropyl betaine, lauryl dimethyl sulfoethyl betaine, stearyl dimethyl sulfopropyl betaine, and mixtures thereof. Amidobetaines and amidosulfobetaines are also contemplated.

Numerous nonionic surfactants can be used in the compositions described herein. Nonionic surfactants useful in the compositions described herein include alkoxylated fatty acid esters, alkyl glucosides, alkyl polyglucosides, amine oxides, alcohol ethoxylates, cocoamine oxide, glyceryl monohydroxystearate, glyceryl stearate, hydroxy stearic acid, lauramine oxide, laureth-2, polyhydroxy fatty acid amides, polyoxyalkylene stearates, propylene glycol stearate, sorbitan monostearate, sucrose cocoate, sucrose esters, sucrose laurate, steareth-2, PEG-40 hydrogenated castor oil, and mixtures thereof. Preferred nonionic surfactants include those based on polyethoxylated sorbitan and oleic acid such as, for example, polysorbate 80 and polysorbate 20, both of which are available under a variety of trade names.

Further nonionic surfactants contemplated herein include, in one aspect, the nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S Surfactants include $C_{11}$-$C_{15}$ secondary alcohol polyethylene glycol ethers. Brij™97 surfactant is Polyoxyethylene(10) oleyl ether; Brij™58 surfactant is polyoxyethylene (20) cetyl ether; and Brij™ 76 surfactant is polyoxyethylene (10) stearyl ether.

In another aspect, a useful class of nonionic surfactants includes the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy)ethanols. Igepal™ CA surfactants include octylphenoxy poly(ethyleneoxy)ethanols. Still another useful class of hydrocarbon nonionic surfactants includes block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. In other aspects, the nonionic surfactants include sorbitan fatty acid esters, polyoxyethylene sorbitan fatty acid esters and polyoxyethylene stearates having HLBs of about 6 to about 19, about 9 to about 18, and about 10 to about 16. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Numerous anionic surfactants can be used herein. In one aspect, the anionic surfactant can be selected from the group comprising alcohol phosphates and phosphonates, alkyl alkoxy carboxylates, alkyl aryl sulfates, alkyl aryl sulfonates, alkyl carboxylates, alkyl ether carboxylates, alkyl ether sulfates, alkyl ether sulfonates, alkyl phosphates, alkyl polyethoxy carboxylates, alkyl polyglucosides, alkyl polyglucoside sulfates, alkyl polyglucoside sulfonates, alkyl succinamates, alkyl sulfates, alkyl sulfonates, aryl sulfates, aryl sulfonates, fatty taurides, isethionates, N-acyl taurates, nonoxynol phosphates, octoxynol phosphates, sarcosinates, sulfated fatty acid esters, taurates, and mixtures thereof. Useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8)N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt. Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the trade name AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo (C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and/or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates. Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340 KL from Clariant Corp., as well as PPG-5 cetyl 10 phosphate available under the trade designation CRODAPHOS™ SG from Croda Inc., Parsipanny, N.J. Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, a surfactant is chosen based on its ability to form a stable emulsion containing an acidic aqueous solution of a polysaccharide and a natural oil polyol. In a further aspect, the concentration of surfactant can be from 0.001% to 1% (v/v), or is about 0.001%, 0.005%, 0.01%, 0.05%, 0.1%, 0.35%, 0.5%, or 1% (v/v) with respect to the final emulsion volume. In another aspect, 0.35% of polysorbate 80 is used. In a further aspect, emulsion formation can be evaluated as function of stirring time (e.g., about 1 minute, about 2 minutes, about 4 minutes, about 6 minutes, about 8 minutes, or about 10 minutes) and/or stirring speed (e.g., about 2,000 rpm, about 5,000 rpm, about 10,000 rpm, or about 20,000 rpm). In one aspect, the polysaccharide is chitosan and emulsions can be formed upon stirring at 10,000 rpm for 2 minutes.

The order in which the polysaccharide, surfactant, and natural oil polyol can be admixed with one another to produce the first admixture can vary. In one aspect, after the polysaccharide/surfactant emulsion is formed, a natural oil polyol can be added to the emulsion. In one aspect, the natural oil polyol is added over time (e.g., 2 minutes, 4 minutes, 5 minutes, 6 minutes, 8 minutes, or 10 minutes) with stirring (2,000 rpm, 5,000 rpm, 10,000 rpm, or 20,000 rpm) to create a final admixture that also incorporates the polysaccharide and the surfactant. In one aspect, the natural oil polyol is castor oil and stirring is conducted at 10,000 rpm for 5 minutes. In one aspect, wherein the surfactant is from 0.001% to 1% (v/v) of the first admixture. In another aspect, the natural oil polyol is from 25% to 70% (v/v) of the first admixture.

Prior to the addition of the polyisocyanate, additional components can be added to the first admixture of polysaccharide, surfactant, and natural oil polyol. In one aspect, a catalyst can be added to the first admixture. A "catalyst" as used herein is any substance that can increase the rate of a chemical reaction. In one aspect, the catalyst is not consumed in the reaction. A single molecule of a catalyst can assist with multiple chemical reactions. Catalysts useful herein include, but are not limited to, tertiary amines such as dimethylethanolamine (DMAE), triethylenediamine (DABCO), 3-aminopropyldimethylamine (DMAPA), dimethylcyclohexylamine (DMCHA); compounds containing hydroxyl groups or secondary amines such as, for example, propylene glycol; metallic compounds including metal carboxylates such as, for example, dibutyltin dilaurate (DBTDL) as well as mercury, lead, bismuth, and zinc carboxylates; and other alkyl tin carboxylates, oxides, and mercaptides. In one aspect, the catalyst is added to an emulsion containing a polysaccharide, a surfactant, and a natural oil polyol at from about 0.05% to about 2% (v/v) with respect to the volume of the emulsion. In another aspect, about 0.05%, 0.1%, 0.15%, 0.2%, 0.25%, 0.4%, 0.6%, 0.7%, 0.8%, 1%, 1.2%, 1.5%, or 2% catalyst is used. In some aspects, a combination of catalysts is used. In one aspect, 0.5% (v/v) dibutyltin dilaurate and 1% (v/v) dimethylethanolamine were used in combination. In a further aspect, stirring is used to incorporate the catalyst throughout an emulsion containing a polysaccharide, a surfactant, and a natural oil polyol. In one aspect, different stirring times (e.g. about 1 minute, about 2 minutes, about 3 minutes, about 4 minutes, about 5 minutes, about 8 minutes, or about 10 minutes) and different stirring speeds (about 100 rpm, about 200 rpm, about 300 rpm, about 400 rpm, about 500 rpm, about 600 rpm, or about 700 rpm) are evaluated to determine the minimum stirring time and speed required to fully incorporate the catalyst into the emulsion. In one aspect, the emulsion and added catalyst are stirred at 300 rpm for 3 minutes.

In another aspect, a clay can be added to the first admixture. "Clay" and "clay minerals" as used herein refer to hydrous aluminum phylosilicates. Clays can optionally include oxides and/or chelates of other metals and semimetals such as, for example, silicon, iron, calcium, magnesium, sodium, potassium, and other alkali and alkaline earth metals. "Bentonite" is a category of impure clay that can consist of montmorillonite, kaolinite, and other species; and that can include potassium, sodium, calcium, aluminum, as well as other metals. "Zeolites" are microporous aluminosilicates that can accommodate a variety of cations, including, but not limited to, sodium, potassium, calcium, and magnesium. The cations in zeolites can be exchanged in aqueous solutions. Clays, bentonites, and zeolites can be used as sources of trace oxides and/or ions in the practice of the present invention. An "oxide" as used herein refers to a molecule, a network solid, or an ionic compound containing at least one oxygen atom and one other element. In one aspect, clays, bentonites, and zeolites contain chelated metal and semimetal ions.

In one aspect, a metal or semimetal oxide or a chelated metal ion can be incorporated into the first admixture. In one aspect, the metal or semimetal oxide includes, for example, $Al_2O_3$, $Fe_2O_3$, MgO, CaO, $Na_2O$, $K_2O$, $SiO_2$, or a combination thereof. In this aspect, the metal or semimetal oxide can be introduced into the polyurethane compositions as a pure compound. In an alternative aspect, ions such as, for example, aluminum, iron (III), magnesium, calcium, sodium, potassium, silicon, and combinations thereof, can be incorporated into the polyurethane compositions described herein through the inclusion of clays or clay minerals. In one aspect, the metal or semimetal oxides or chelated metals are incorporated at concentrations of from about 0.02 nM to about 1.2 mM, or at 0.2 nM, 0.04 nM, 0.06 nM, 0.08 nM, 0.1 nM, 0.15 nM, 0.2 nM, 0.25 nM, 0.3 nM, 0.35 nM, 0.4 nM, 0.45 nM, 0.5 nM, 0.55 nM, 0.2 mM, 0.4 mM, 0.6 mM, 0.8 mM, or 1.2 mM.

In another aspect, one or more water-soluble metal salts can be incorporated into the first admixture. In one aspect, the water-soluble metal salts can include, for example, gallium (III) nitrate hydrate, zinc sulfate, zinc acetate, or a combination thereof. In one aspect, 50 mg/L of gallium (III) nitrate hydrate is incorporated into the emulsion containing polysaccharide, surfactant, and natural oil polyol. In another aspect, 100 mg/L of zinc sulfate is incorporated into the emulsion containing polysaccharide, surfactant, and natural oil polyol.

In one aspect, the first admixture is prepared by admixing chitosan (polysaccharide), a solvent comprising 0.05N to 0.15 aqueous HCl, polysorbate 80 (surfactant), and castor oil (natural oil polyol). In another aspect, the first admixture is produced by admixing chitosan, polysorbate 80, microcrystalline cellulose, bentonite, zeolite, castor oil, dibutyltin dilaurate, and N,N-dimethylaminoethanol.

In another aspect, the first admixture is prepared by admixing 50% (v/v) of a solution of 4% chitosan in 0.1N HCl, 0.35% (v/v) polysorbate 80, 2% (w/v) microcrystalline cellulose, 0.2% (w/v) bentonite, 0.2% (w/v) zeolite, 47.5% (v/v) castor oil, 0.2% (v/v) dibutyltin dilaurate, and 1% (v/v) N,N-dimethylaminoethanol.

After preparation of the first admixture as described above, a polyisocyanate is added to the first admixture. "Polyisocyanates" as used herein are compounds with two or more —N=C=O groups. In one aspect, the polyisocyanate is an aliphatic diisocyanate, a cycloaliphatic diisocyanate, an aromatic diisocyanate, or an isomer thereof. In another aspect, the isocyanate or polyisocyanate is 2,4-toluenediisocyanate alone or in combination with an isomer thereof (TDI), 4,4'-methylene diphenyl diisocyanate (MDI), 4,4'-methylenebis(cyclohexylisocyanate) (H12-MDI), 1-isocyanato-3-isocyanato-methyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethylxylylenediisocyanate (TMXDI), or any combination thereof. The isocyanate or polyisocyanate can exist as one or more structural isomers. Alternatively, the isocyanate or polyisocyanate can be a dimer, trimer, or oligomer. In other aspects, the isocyanate or polyisocyanate can exist as one or more positional isomers. For example, the polyisocyanate can be a mixture of 2,4-toluenediisocyanate and 2,6-toluenediisocyanate. In a further aspect, the polyisocyanate can be a 65:35 mixture of 2,4-TDI and 2,6-TDI (i.e., TDI 65). In a different aspect, the polyisocyanate can be an 80:20 mixture of 2,4-TDI and 2,6-TDI (i.e., TDI 80). In an alternative aspect, the polyisocyanate is a modified MDI or polyphenylmethane polyisocyanate such as one of those sold by Yantai Wanhua Polyurethanes Co. under the trade name WANNATE®.

In one aspect, the polyisocyanate is added to the first admixture at different ratios such as, for example, about 1:1, about 1:2, about 1:3, about 1:4, about 1:5, about 1:6, about 1:7, or about 1:8 with respect to the total emulsion volume. In this aspect, polymerization reactions can then be carried out. Different reaction times (e.g. 8 minutes, 10 minutes, 12 minutes, 15 minutes, or 20 minutes) and stirring speeds (e.g., 500 rpm, 600 rpm, 700 rpm, 800 rpm, 900 rpm, or 1000 rpm) can be evaluated to determine the optimum reaction time and stirring speed. In one aspect, the first admixture is admixed with the polyisocyanate for 10 minutes at 500 rpm. In another aspect, the reaction is conducted at room temperature.

Upon admixing the components in the first admixture with the polyisocyanate, isocyanate-reactive functional groups present on the polysaccharide, surfactant, and/or natural oil polyol react with the isocyanate groups on the polyisocyanate to produce a polyurethane. Here, a polymer composed of organic residues joined by urethane linkages is produced. Although the components in the first admixture include hydroxyl groups, other components may be present that include other isocyanate-reactive functional groups an amine groups, a thiol groups, or other nucleophilic groups capable of reacting with isocyanate groups.

In one aspect, the polyurethane composition is prepared by admixing chitosan (polysaccharide), a solvent comprising 0.05N to 0.15 aqueous HCl, polysorbate 80 (surfactant), and castor oil (natural oil polyol); and polymerizing the first admixture by adding MDI to the first admixture. In another aspect, the polyurethane composition is produced by admixing chitosan, polysorbate 80, microcrystalline cellulose, bentonite, zeolite, castor oil, dibutyltin dilaurate, and N,N-dimethylaminoethanol; and polymerizing the first admixture by adding MDI to the first admixture.

In another aspect, the polyurethane composition is prepared by admixing 50% (v/v) of a solution of 4% chitosan in 0.1N HCl, 0.35% (v/v) polysorbate 80, 2% (w/v) microcrystalline cellulose, 0.2% (w/v) bentonite, 0.2% (w/v) zeolite, 47.5% (v/v) castor oil, 0.2% (v/v) dibutyltin dilaurate, and 1% (v/v) N,N-dimethylaminoethanol; and polymerizing the first admixture by adding MDI to the first admixture at a ratio of 1 part MDI to 5 parts first admixture.

The polyurethane compositions produced herein can be used to produce biofoams that have numerous applications. The term "biofoam" as used herein is any substance formed when pockets of gas have been trapped in a solid or liquid. In one aspect, the biofoams produced herein can exist as an emulsion or dispersion at room temperature. In other aspects, he biofoams produced herein are solid materials at room temperature.

The selection and amounts of reactants as well as processing conditions will determine the physical state of the biofoams. In one aspect, when the polyisocyanate is admixed with the first admixture, a solid biofoam is produced.

In other aspects, one or more blowing agents can be incorporated into the polyurethane compositions to produce the biofoams. A blowing agent can be physical or chemical in nature. A "physical blowing agent" is a gas or low boiling point liquid which expands due to heat generated by the polyurethane-forming reaction, thus forming bubbles and creating foam. A "chemical blowing agent" is a compound or substance that reacts to form a gas. In one aspect, the blowing agent is a physical blowing agent. Physical blowing agents include compounds such as, for example, hydrofluorocarbons (HFCs), hydrocarbons (HCs), hydrofluoroolefins, liquid $CO_2$, and other low boiling point liquids. In one aspect, the physical blowing agent is HFC-134a (1,1,1,2-tetrafluoroethane), HFC-245fa (pentafluoropropane), HFC-365mfc (1,1,1,3,3-pentafluorobutane), HFC-152a (1,1-difluoroethane), formic acid, methyl formate, HFO-1234ze (1,3,3,3-tetrafluoropropene), cyclopentane, n-pentane, isopentane, iso-butane, acetone, dichloromethane, or a mixture thereof. In another aspect, the blowing agent is a chemical blowing agent. In one aspect, the chemical blowing agent is carbon dioxide produced by the reaction of isocyanate groups with water. In a further aspect, both chemical and physical blowing agents can be used.

In another aspect, after the preparation of the biofoam, the biofoam can contain residual solvent (e.g., water). In certain aspects, it is desirable to remove all or substantially all (e.g., greater than 70%, greater than 80%, greater than 90%, greater than 95%, greater than 99%, or 100%) of the solvent in the biofoam. In one aspect, drying of the biofoams can be accomplished in an oven at about 20° C., 30° C., 40° C., 50° C., 60° C., or about 70° C. In one aspect, the biofoams are dried in an oven at 50° C. In a further aspect, the biofoams can be dried for from about 0.5 to about 100 hours, or for about 72 hours. In one aspect, removal of water from biofoams is assessed by periodically removing the biofoams from the oven and weighing them. When the biofoams have the same weight at, for example, at least 2 or 3 successive weighings separated by several hours, the biofoams can be considered to be dry and can be removed from the oven.

The biofoams described herein can be produced in any desired shape or size. For example, the polyurethane composition can be poured into a mold. If necessary, the mold containing the polyurethane composition can be placed in an oven to remove residual solvent and produce the final biofoam.

In other aspects, the biofoams include additional additives not already described above such as, for example, flame retardants, color additives, release agents, biocides, other additives, or a combination thereof. The additional components can be admixed with a dispersion or emulsion of polyurethane composition in order incorporate the additives throughout the biofoam. In the alternative, the additives can be applied to the surface of the solid biofoam.

The biofoams produced herein have several beneficial properties. In one aspect, the biofoams are resistant to discoloration. In one aspect, discoloration of the biofoams can be assessed by exposing the biofoams to an agent known to cause stains. In a further aspect, the agent known to cause stains is, for example, tea, coffee, or red wine. In one aspect, the biofoams are submersed in coffee for a period of up to about 24 hours. In this aspect, after 24 hours, the biofoams are removed from the coffee and rinsed with water. Discoloration can then be qualitatively assessed as, for example, weak, medium, or strong.

In another aspect, the biofoams are resistant to acid degradation. For example, the biofoam can be assessed by placing a piece of the foam in an aqueous solution of an acid for 24 or 48 hours. In a further aspect, the acid is present at a 0.1N concentration. In another aspect, the acid is an organic acid such as, for example, acetic acid or formic acid. In an alternative aspect, the acid is an inorganic acid such as, for example, nitric acid, hydrochloric acid, phosphoric acid, or sulfuric acid. Resistance to mixtures of acids can also be tested. In a further aspect, photographs of the foam before and after exposure to acid can be compared to qualitatively assess acid resistance. In another aspect, the foam can be weighed before and after acid exposure to assess whether material has been lost.

In one aspect, it is desirable to know the maximum temperature to which the biofoams can be exposed without decomposition. This is known as temperature resistance. In one aspect, decomposition due to heat exposure can be assessed by placing a piece of the foam in an oven at a temperature of from about 50° C. to about 120° C. In a further aspect, temperature resistance is assessed at about 50° C., at about 80° C., or at about 120° C. In certain aspects, pieces of biofoam can be placed in an oven and the internal temperatures of the biofoam pieces can be measured periodically with, for example, a thermometer or a thermocouple. In a further aspect, temperature resistance can be measured every 10 minutes for up to one hour. In one aspect, the biofoam samples can be weighed prior to assessing temperature resistance, and can be weighed periodically to evaluate the level of decomposition. In this aspect, samples can be weighed every 10 minutes for up to one hour, at about the same time the internal temperature of the biofoam pieces is being measured, with weight loss indicating that decomposition has occurred. In an additional aspect, temperature resistance can be qualitatively assessed by, for example, visually noting any discoloration of the biofoam samples that occurs subsequent to heat treatment. In one aspect, if a sample exhibits less than about 20% weight loss, or less than about 10% weight loss, after exposure to a particular temperature, the sample can be said to be temperature resistant. In another aspect, if a sample does not become visibly discolored after exposure to a particular temperature, the sample can be said to be temperature resistant.

In one aspect, it is desirable to assess the biofoams of the present invention for recovery from deformation. In this aspect, pressure can be applied to the biofoams, causing deformation. Also in this aspect, when pressure is removed from the biofoams, the biofoams can return to their original shapes and/or sizes. In certain aspects, from about 0.5 bars to about 1 bar of pressure are applied. In other aspects, the time required for the biofoams to recover from deformation is measured. In one aspect, the biofoams take up to about 5 seconds to recover from deformation. In another aspect, the biofoams take from about 1 second to about 3 seconds to recover from deformation.

The biofoams produced herein can be used in any application where synthetic polyurethane foams are used. For example, the biofoams can be used in upholstery such as cushions, pillows, or mattresses. In other aspects, the biofoams can be used as an insulator in building products, automobiles, or aircraft.

EXAMPLES

The following examples are put forth so as to provide those of ordinary skill in the art with a complete disclosure and description of how the compositions and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions that can be used to optimize the product purity and yield obtained from the described process. Only reasonable and routine experimentation will be required to optimize such process conditions.

Optimization of Reaction Components

Several grades of chitosan were obtained that were 50% acetylated, 60% acetylated, and 77% acetylated. Solutions of chitosan were prepared in 1% (v/v) aqueous acetic acid at concentrations of 0.01%, 0.02%, 0.05%, 0.1%, 0.5%, 1%, 1.5%, 2%, 2.5%, 3%, 3.5%, 4%, 4.5%, 5%, 5.5%, and 6% (w/v) chitosan. For most polymerization experiments, 2% and 4% solutions of chitosan were used. Chitosan solutions were also prepared using 2% hydrochloric acid, 1% formic acid, 1% nitric acid, and 1% sulfuric acid. Of these, the hydrochloric acid solution had the most desirable properties; further experiments were performed to determine the optimum concentration of HCl. Concentrations including 1%, 1.4%, 2%, 2.4%, 3%, 3.4%, 4%, and 4.5% (v/v) aqueous HCl were tested. Of these, the 1.4% solution of HCl had the most desirable properties. All acidic chitosan solutions were shaken at 200 rpm overnight to ensure adequate mixing had occurred.

Different surfactants were evaluated for their abilities to form stable emulsions of the acidic chitosan solutions. In particular, polysorbate 80, polysorbate 20, soy lecithin, alcohol ethoxylates, and PEG 40 castor oil were tested. Surfactants were tested over a range of concentrations including 0.001%, 0.005%, 0.01%, 0.05%, 0.1%, 0.35%, 0.5%, and 1% (v/v). Use of 0.35% polysorbate 80 resulted in the formation of particularly stable emulsions. Emulsion formation was evaluated as a function of stirring time (1, 2, 4, 6, 8, or 10 minutes) and stirring speed (2,000; 5,000; 10,000; or 20,000 rpm), with 2 minutes of stirring at 10,000 rpm chosen for future experiments.

Several vegetable oils and fatty acids containing primary and/or secondary hydroxyl groups were added to the emulsions containing surfactants and chitosan in acidic aqueous solution. These included castor oil, ricinoleic acid, coriolic acid, and several chemically-modified fatty acids. These oils and/or fatty acids were added slowly to the chitosan-containing solution with stirring (2,000; 5,000; 10,000; or 20,000 rpm) over time (2, 4, 5, 6, 8, or 10 minutes) to create a final admixture. Castor oil was chosen for future experiments, with stirring at 10,000 rpm for 5 minutes to create emulsions with the solutions containing chitosan and surfactants.

In some experiments, additional compounds were added to the chitosan solutions to increase the availability of the chitosan's isocyanate-reactive groups (e.g., hydroxyl groups) for polyurethane-forming reactions. These compounds included cellulose and guar. Cellulose was used at concentrations of 0.1%, 0.2%, 0.4%, 0.5%, 0.6%, 1%, 1.5%, 2%, 2.5%, 3%, 3.5%, 4%, and 5% (w/v) of the final admixture containing chitosan, surfactant, and castor oil. Guar was used at concentrations of 0.001%, 0.005%, 0.01%, 0.025%, 0.05%, 0.1%, 0.2%, 0.4%, 0.6%, 0.7%, and 1% (w/v) of the final admixture. Microcrystalline cellulose at 2% (w/v) was used for most experiments.

The effects of metal ions and oxides of metals and/or semimetals on the polyurethane biofoams of the present invention were also explored. Metal and/or semimetal oxides including $Al_2O_3$, $Fe_2O_3$, MgO, $Ca_2O$, $Na_2O$, $K_2O$, and $SiO_2$ were introduced to the compositions and mixtures described herein at concentrations of between 0.02, 0.04, 0.06, 0.08, 0.1, 0.15, 0.2, 0.25, 0.3, 0.35, 0.4, 0.45, 0.5, or 0.55 nM (lower endpoint) and 0.2, 0.4, 0.6, 0.8, or 1.2 mM (upper endpoint). Alternatively, aluminum, iron (III), magnesium, calcium, sodium, potassium, and silicon were introduced as components of bentonite and zeolite clay minerals. Additional individual cations were added via the incorporation of gallium (III) nitrate hydrate, zinc sulfate, or zinc acetate. For most experiments, bentonite and zeolite, gallium (III) nitrate hydrate, and zinc sulfate were used.

Multiple catalysts and catalyst combinations were evaluated for their abilities to promote polyurethane formation using the reactants described above. These include dibutyltin dilaurate, dimethylethanolamine, triethylene diamine, dipropylene glycol, and 3-aminopropyldimethylamine Various concentrations of catalyst were added to reaction mixtures including 0.05%, 0.1%, 0.15%, 0.2%, 0.25%, 0.4%, 0.6%, 0.7%, 0.8%, 1%, 1.2%, 1.5%, and 2% (v/v). For most experiments, a combination of 0.5% (v/v) dibutyltin dilaurate and 1% (v/v) dimethylethanolamine was used. Incorporation of catalyst into the castor oil/chitosan emulsions required stirring. Different stirring speeds (i.e. 100, 200, 300, 400, 500, 600, and 700 rpm) and times (i.e., 1, 2, 3, 4, 5, 8, and 10 minutes) were evaluated, with stirring at 300 rpm for 3 minutes being used for most experiments.

Different isocyanates were reacted with the emulsions containing chitosan, castor oil, surfactant, and catalyst. Miscibility/emulsifiability of the isocyanate with the existing emulsions was preferable. 4,4'-methylene diphenyl diisocyanate (MDI), a 65:35 mixture of 2,4-toluene diisocyanate and 2,6-toluenediisocyanate (TDI 65), an 80:20 mixture of 2,4-toluene diisocyanate and 2,6-toluenediisocyanate (TDI 80), and a modified MDI (Wannate 8001, consisting of a polyol-modified diphenylmethane diisocyanate and polyphenylmethane polyisocyanate) were evaluated, with MDI chosen for subsequent experiments. Polymerization reactions were performed using different ratios of isocyanate to emulsion to evaluate the resultant foams; these included 1:1, 1:2, 1:3, 1:4, 1:5, 1:6, 1:7, and 1:8. A 1:5 isocyanate:emulsion ratio was used in most experiments. Reactions occurred at room temperature with stirring. Different reaction times (8, 10, 12, 15, or 20 minutes) and stirring speeds (500, 600, 700, 800, 900, or 1000 rpm) were evaluated, with stirring at 500 rpm for 10 minutes being used for most experiments.

Procedure

The following general procedure was used to prepare polyurethane biofoams.
1. 77% acetylated chitosan was dissolved in 0.1N HCl at a 4% (w/v) concentration. The mixture was stirred at 200 rpm overnight to ensure complete dissolution.
2. Polysorbate 80 was added to the chitosan solution in a concentration equivalent to 0.35% (v/v) of the final emulsion volume. This was stirred for 2 minutes at 10,000 rpm to generate an initial emulsion.
3. Castor oil was added over time to the initial emulsion with stirring at 10,000 rpm for 5 minutes to generate the final emulsion.
4. Microcrystalline cellulose, if used, was next added to the final emulsion. Cellulose was generally added at a concentration of 2% (w/v).
5. Metal and/or semimetal oxides, if used, were next added to the final emulsion, either as pure compounds or as components of zeolites and bentonites.
6. Gallium and/or zinc ions, if used, were next added to the final emulsion as gallium (III) nitrate hydrate and zinc sulfate, respectively.
7. 0.2% (v/v) dibutyltin dilaurate and 1% N,N-dimethylethanolamine were added to the final emulsion. This was stirred at 300 rpm for 3 minutes to incorporate these catalyst compounds uniformly throughout the emulsion.
8. MDI was added to the emulsion in a ratio of 1:5 MDI:(sum of all other components). This was stirred at 500 rpm for 10 minutes to generate a polyurethane biofoam. If the mechanical properties of the foam were to be further probed, this step was carried out in a mold.

Reaction Compositions

The abbreviations listed in Table 1 are used throughout the Examples.

TABLE 1

| | Abbreviations |
|---|---|
| TDI | Toluene diisocyanate (65/35 mix of 2,4- and 2,6-isomers) |
| MDI | Methylene diphenyl diisocyanate |
| DABCO | 1,4-diazabicyclo[2.2.2]octane or triethylenediamine |
| DBTDL | Dibutyltin dilaurate |
| DMAPA | Dimethylaminopropylamine or 3-aminopropyldimethylamine |
| DMAE | N,N-dimethylethanolamine or dimethylaminoethanol |

Figure 2:
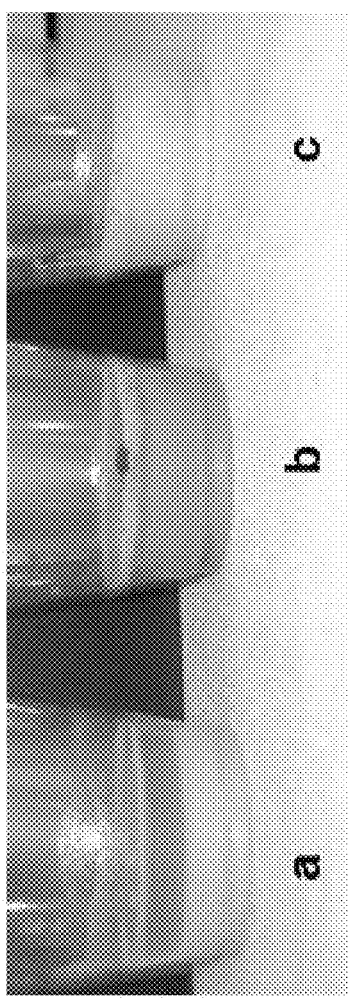
FIG. 2 shows mixtures of powdered chitosan and various isocyanates: (a) TDI 65, (b) MDI, (c) Wannate 8001 in a 5:1 ratio.

Various surfactants and isocyanates were tested for miscibility with chitosan. Mixtures of soy lecithin and chitosan solutions separated into two phases after 72 hours while mixtures of chitosan with polysorbate 20 or polysorbate 80 remained as a single phase during the same time frame (FIG. 1). A mixture of TDI 65 and isocyanate separated into two phases. WANNATE 8001 (a modified MDI) and MDI were miscible with chitosan over time (FIG. 2). Further, chitosan concentration in the reaction mixtures was varied to determine the optimum amount of chitosan to use. Additionally, different catalysts were evaluated for their abilities to assist in the polymerization of biofoam. Results are presented in Table 2.

TABLE 2

Optimization of Isocyanate, Catalyst, and Chitosan Concentration

| | | | Isocyanate[a] | | | Catalyst[b] | | | | | |
|---|---|---|---|---|---|---|---|---|---|---|---|
| Mixture | Chitosan[c] | Water[d] | TDI | MDI | WANNATE | HOAc | DABCO | DBTDL | DMAPA | DMAE | Dipropylene Glycol |
| 1 | P | | 1:5 | | | | | | | | |
| 2 | P | | | 1:5 | | | | | | | |
| 3 | P | | | | 1:5 | | | | | | |
| 4 | 2% | aq | | 1:5 | | 0.1N | | | | | |
| 5 | 2% | aq | | 1:5 | | 0.1N | 0.2% | | | | 0.2% |
| 6 | 2% | aq | | 1:5 | | 0.1N | | 0.2% | | | |
| 7 | 2% | aq | | 1:5 | | 0.1N | | | 0.2% | | |
| 8 | 2% | aq | | 1:5 | | 0.1N | | | | 0.2% | |
| 9 | 4% | aq | | 1:5 | | 0.1N | | | | | |
| 10 | 4% | aq | | 1:5 | | 0.1N | 0.2% | | | | |

[a]Ratio of isocyanate to sum of other reaction components.
[b]Catalyst percentages are (v/v).
[c]Symbol "P" indicates solid (powdered) chitosan; no concentration available.
[d]Symbol "aq" indicates aqueous solution.

Figure 3:
FIG. 3 shows a mixture of MDI and 2% chitosan in 0.1N acetic acid in a 1:5 ratio.
Figure 4:
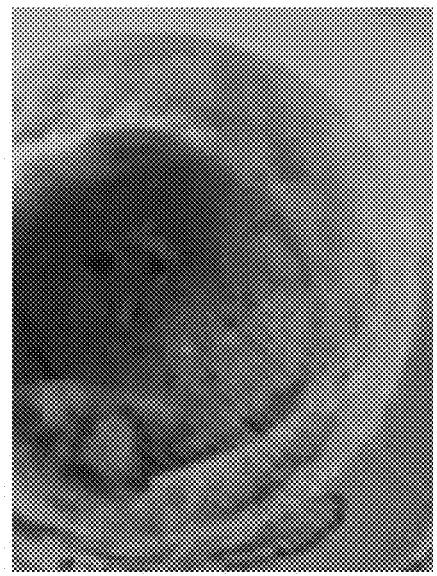
FIG. 4 shows the polyurethane produced by reacting 2% chitosan in 0.1N acetic acid with MDI using 0.2% v/v of triethylene diamine and dipropylene glycol as catalysts.
Figure 5:
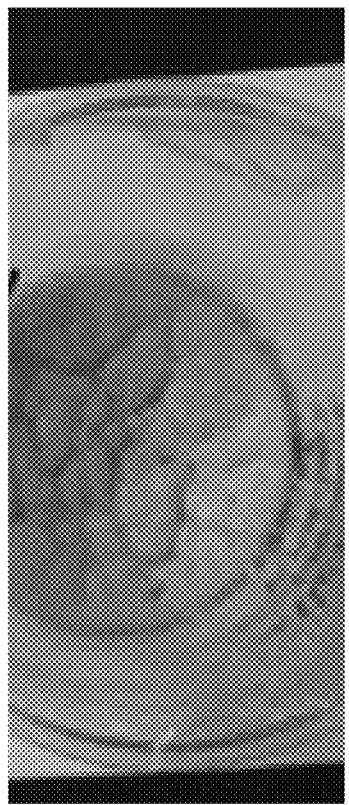
FIG. 5 shows the polyurethane produced by reacting 2% chitosan in 0.1N acetic acid with MDI using 0.2% v/v of dibutyltin dilaurate as catalyst.
Figure 6:
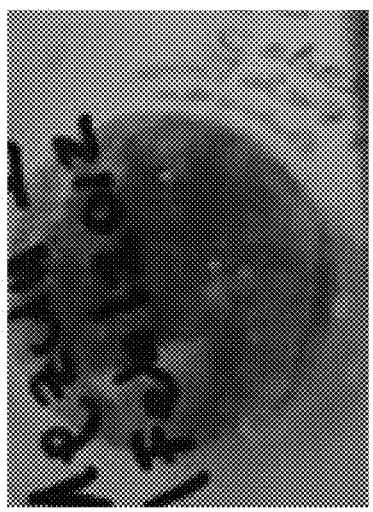
FIG. 6 shows the polyurethane produced by reacting 2% chitosan in 0.1N acetic acid with MDI using 0.2% v/v of 3-aminopropyldimethylamine as catalyst.
Figure 7:
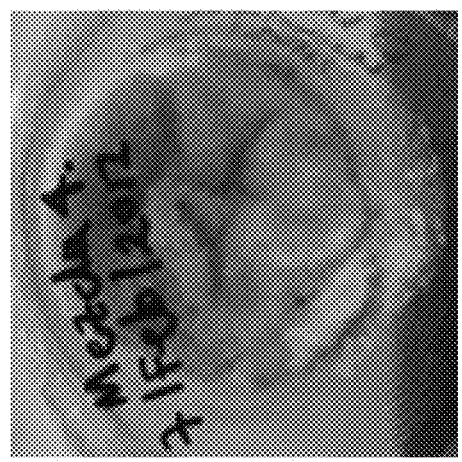
FIG. 7 shows the polyurethane produced by reacting 2% chitosan in 0.1N acetic acid with MDI using 0.2% v/v of N,N-dimethylethanolamine as catalyst.
Figure 8:
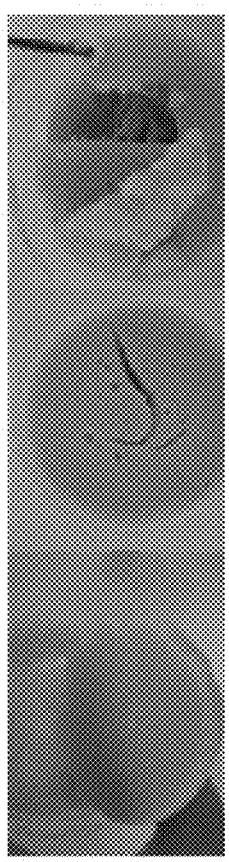
FIG. 8 shows several views of a sub-product that formed when 4% chitosan in 0.1N acetic acid was reacted with MDI.
Figure 9:
FIG. 9 shows the polyurethane produced by reacting 4% chitosan in 0.1N acetic acid with MDI using 0.2% v/v of dibutyltin dilaurate as catalyst.
Figure 10:
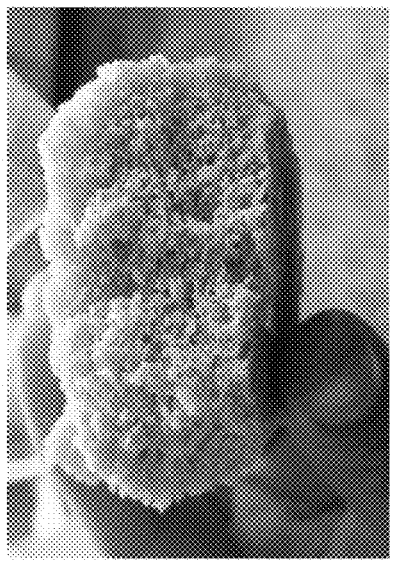
FIG. 10 shows a cross section of the polyurethane produced by reacting 4% chitosan in 0.1N acetic acid with MDI using 0.2% v/v of dibutyltin dilaurate as catalyst.

Mixture 4, which lacked a catalyst, resulted in an inferior, unpolymerized or partially polymerized product (FIG. 3). Reactions involving mixtures 5-10 produced colored foams of varying qualities (FIGS. 4-10).

Castor oil, with and without catalysts and a surfactant, was added to the aqueous chitosan solutions already described. Representative compositions are presented in Table 3.

TABLE 3

Addition of Castor Oil and Surfactant

| Mixture | % Chitosan in 0.1N HOAc | % Aqueous Solution in Mixture[a] | MDI[b] | DBTDL | DMAE | % Castor Oil | % Polysorbate 80 |
|---|---|---|---|---|---|---|---|
| 11 | 4 | 30 | 1:5 | | | 70 | |
| 12 | 4 | 41.15 | 1:5 | 0.17% | 0.8% | 40.89 | 0.29 |

[a]Aqueous solution is 4% chitosan in 0.1N acetic acid.
[b]Ratio of MDI to sum of other components.

Figure 11:
FIG. 11 shows the polyurethane produced by reacting MDI with 70% castor oil and 30% of a 4% solution of chitosan in 0.1N acetic acid.
Figure 12:
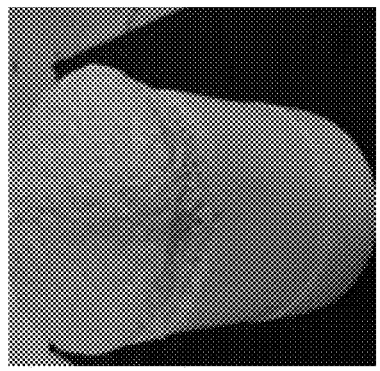
FIG. 12 shows a flexible biofoam produced by reacting 0.29% polysorbate 80; 41.15% of a 4% aqueous solution of chitosan; 40.89% castor oil; 0.8% of N,N-dimethylethanolamine; 0.17% of dibutyltin dilaurate, and 16.7% of MDI.
Figure 13:
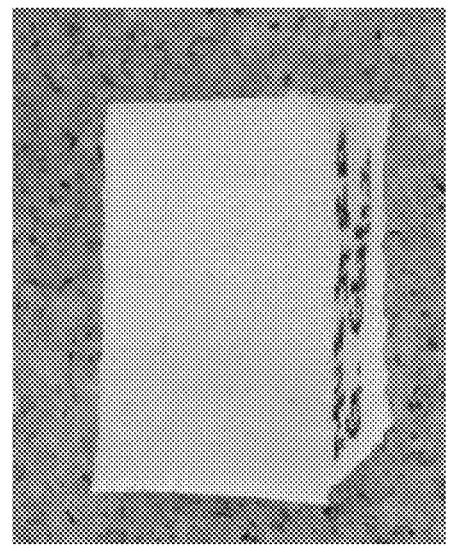
FIG. 13 shows a flexible biofoam after oven drying at 50° C.

Reacting the components of Mixture 11 resulted in some polymerization but the product was of inferior quality (FIG. 11). Polymerization of Mixture 12 resulted in the formation of a flexible biofoam with a cream time of 120 seconds, a tack-free time of 312.6 seconds, and a gel time of 540 seconds (FIGS. 12 and 13).

Biofoams were synthesized using different proportions of aqueous chitosan solution and castor oil were prepared. Representative compositions are provided in Table 4.

TABLE 4

Optimization of Castor Oil Concentration

| Mixture | % Aqueous Solution[a] in Mixture | % Castor Oil | % Polysorbate 80 |
|---|---|---|---|
| 13 | 55 | 44.65 | 0.35 |
| 14 | 60 | 39.65 | 0.35 |
| 15 | 65 | 34.65 | 0.35 |
| 16 | 70 | 29.65 | 0.35 |

[a]Aqueous solution is 4% chitosan in water.

The effects of various additives, including HCl, guar, and different types of surfactant (i.e., polysorbate 80 and polysorbate 20) on biofilm formation were also evaluated. Representative compositions are provided in Table 5.

TABLE 5

Optimization of Guar Concentration and Determination of Acid and Surfactant

| Mixture | % Aqueous Solution[a] in Mixture | HCl | % Castor Oil | % Guar | % Polysorbate 80 | % Polysorbate 20 |
|---|---|---|---|---|---|---|
| 17 | 50 | | 44.65 | 5 | 0.35 | |
| 18 | 50 | | 39.65 | 10 | 0.35 | |
| 19 | 50 | | 34.65 | 15 | 0.35 | |
| 20 | 50 | | 29.65 | 20 | 0.35 | |
| 21 | 60 | | 39.65 | | | 0.35 |
| 22 | 65 | | 34.65 | | | 0.35 |
| 23 | 50 | 0.1N | 49.65 | | 0.35 | |
| 24 | 50 | 0.1N | 49.55 | 0.1 | 0.35 | |
| 25 | 50 | 0.1N | 49.15 | 0.5 | 0.35 | |
| 26 | 50 | 0.1N | 49.55 | 0.1 | 0.35 | |
| 27 | 50 | 0.1N | 49.6 | 0.05 | 0.35 | |
| 28 | 50 | 0.1N | 49.625 | 0.025 | 0.35 | |

[a]Aqueous solution is 4% chitosan in water or HCl, as indicated.

Biofoam samples were prepared incorporating soluble zinc and gallium salts along with either cellulose or metal/semimetal oxides (sourced from clay minerals). Representative compositions are presented in Table 6.

TABLE 6

Optimization of Cellulose, Metal, and Oxide Concentrations

| Mixture | % Aqueous Solution[a] in Mixture | % Castor Oil | % Cellulose | % Polysorbate 80 | mg/L Ga(NO$_3$)$_3$·xH$_2$O | mg/L ZnSO$_4$·7H$_2$O | Oxide Content[b] |
|---|---|---|---|---|---|---|---|
| 29 | 50 | 47.65 | 2 | 0.35 | 50 | | |
| 30 | 50 | 47.65 | 2 | 0.35 | | 100 | |
| 31 | 50 | 47.65 | 2 | 0.35 | 50 | 100 | |
| 32 | 50 | 47.65 | 2 | 0.35 | | | |
| 33 | 50 | 49.55 | | 0.35 | | 100 | Dilution A |
| 34 | 50 | 49.55 | | 0.35 | 50 | | Dilution A |
| 35 | 50 | 49.55 | | 0.35 | 50 | 100 | Dilution A |
| 36 | 50 | 49.55 | | 0.35 | | | Dilution A |
| 37 | 50 | 49.56 | | 0.35 | | 100 | Dilution B |
| 38 | 50 | 49.56 | | 0.35 | 50 | | Dilution B |
| 39 | 50 | 49.56 | | 0.35 | 50 | 100 | Dilution B |
| 40 | 50 | 49.56 | | 0.35 | | | Dilution B |

[a]Aqueous solution consists of 4% chitosan in 0.1N HCl.
[b]Dilution A: 0.063% SiO$_2$, 0.0135% Al$_2$O$_3$, 0.0045% Fe$_2$O$_3$, 0.00295% CaO, 0.00295% MgO, 0.0009% Na$_2$O, 0.0032% K$_2$O. Dilution B: 0.06147% SiO$_2$, 0.01425% Al$_2$O$_3$, 0.00238% Fe$_2$O$_3$, 0.0015% CaO, 0.00147% MgO, 0.00147% Na$_2$O, 0.00084% K$_2$O.

Biofoam samples were also prepared with similar compositions to those shown in Table 6 but incorporating cellulose as well as metal/semimetal oxides (sourced from clay minerals). Representative compositions are presented in Table 7.

TABLE 7

Further Optimization of Metal and Oxide Concentrations

| Mixture | % Aqueous Solution Mixture[a] | % Castor Oil | % Cellulose | % Polysorbate 80 | mg/L Ga(NO$_3$)$_3$·xH$_2$O | mg/L ZnSO$_4$·7H$_2$O | Oxide Content[b] |
|---|---|---|---|---|---|---|---|
| 41 | 50 | 47.55 | 2 | 0.35 | | 100 | Dilution A |
| 42 | 50 | 47.55 | 2 | 0.35 | 50 | | Dilution A |
| 43 | 50 | 47.55 | 2 | 0.35 | 50 | 100 | Dilution A |
| 44 | 50 | 47.55 | 2 | 0.35 | | | Dilution A |
| 45 | 50 | 47.56 | 2 | 0.35 | | 100 | Dilution B |
| 46 | 50 | 47.56 | 2 | 0.35 | 50 | | Dilution B |
| 47 | 50 | 47.56 | 2 | 0.35 | 50 | 100 | Dilution B |
| 48 | 50 | 47.56 | 2 | 0.35 | | | Dilution B |
| 49 | 50 | 47.47 | 2 | 0.35 | | 100 | Dilution C |
| 50 | 50 | 47.47 | 2 | 0.35 | 50 | | Dilution C |
| 51 | 50 | 47.47 | 2 | 0.35 | 50 | 100 | Dilution C |
| 52 | 50 | 47.47 | 2 | 0.35 | | | Dilution C |

[a]Aqueous solution consists of 4% chitosan in 0.1N HCl.
[b]Dilution A: 0.063% SiO$_2$, 0.0135% Al$_2$O$_3$, 0.0045% Fe$_2$O$_3$, 0.00295% CaO, 0.00295% MgO, 0.0009% Na$_2$O, 0.0032% K$_2$O. Dilution B: 0.06147% SiO$_2$, 0.01425% Al$_2$O$_3$, 0.00238% Fe$_2$O$_3$, 0.0015% CaO, 0.00147% MgO, 0.00147% Na$_2$O, 0.00084% K$_2$O. Dilution C: 0.12% SiO$_2$, 0.023% Al$_2$O$_3$, 0.0044% Fe$_2$O$_3$, 0.0069% CaO, 0.0028% MgO, 0.0044% Na$_2$O, 0.0040% K$_2$O.

Biofoam samples were also prepared with similar compositions to those shown in Table 7 but omitting both the cellulose and the metal/semimetal oxides (sourced from clay minerals). Representative compositions are presented in Table 8.

TABLE 8

Optimized Mixtures with Oxides Omitted

| Mixture | % Aqueous Solution[a] in Mixture | % Castor Oil | % Polysorbate 80 | mg/L Ga(NO$_3$)$_3$·xH$_2$O | mg/L ZnSO$_4$·7H$_2$O |
|---|---|---|---|---|---|
| 53 | 50 | 49.65 | 0.35 | | 100 |
| 54 | 50 | 49.65 | 0.35 | 50 | |
| 55 | 50 | 49.65 | 0.35 | 50 | 100 |

[a]Aqueous solution consists of 4% chitosan in 0.1N HCl.

Figure 14:
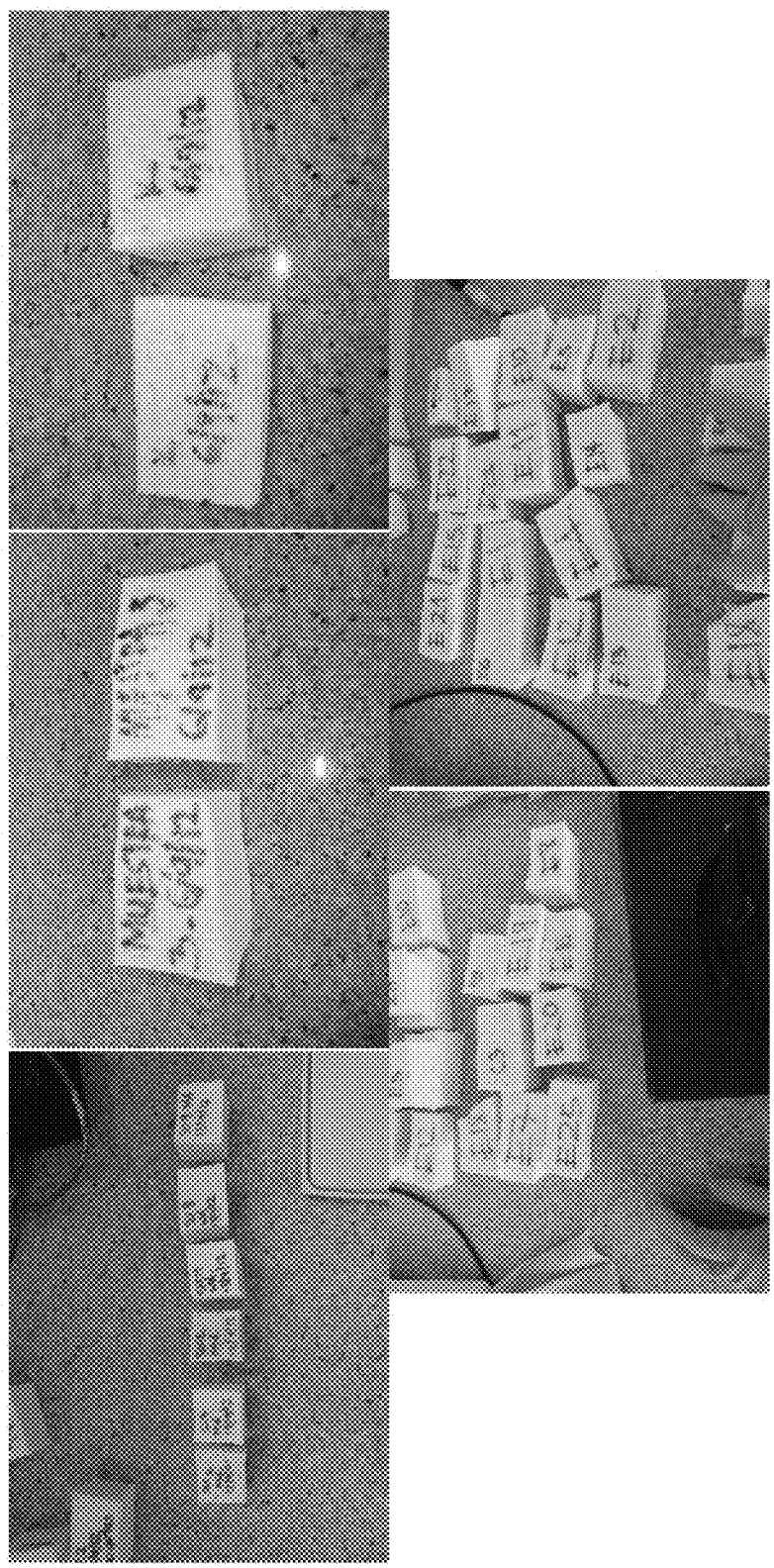
FIG. 14 shows various biofoams of the present invention.

0.2% dibutyltin dilaurate and 1% DMAE were added to each of compositions 13-55. This admixture was then reacted with MDI in a ratio of 5:1 (admixture:MDI). Representative biofoams are shown in FIG. 14.

Figure 15:
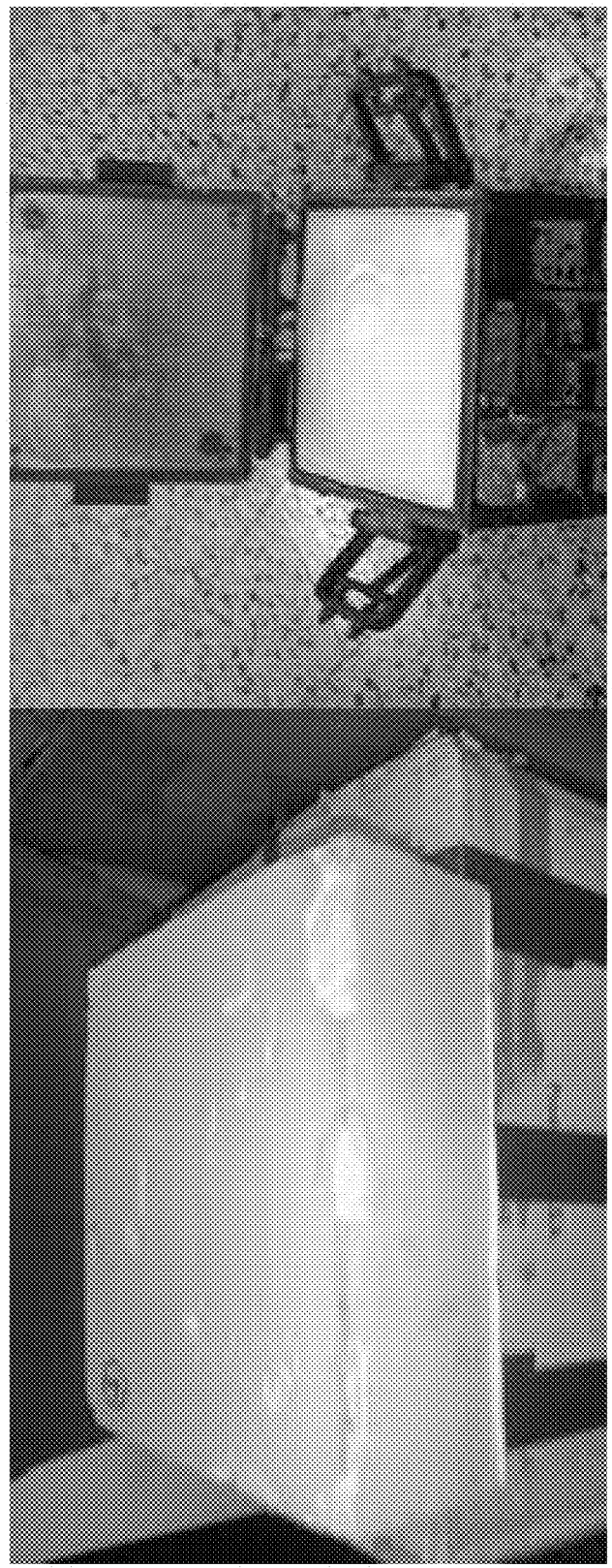
FIG. 15 shows (right) a mold used to prepare biofoams and (left) a biofoam prepared in and released from the mold.

For purposes of characterization of the physical, chemical, and mechanical properties of the biofoams, some biofoam samples were polymerized in a mold to produce a uniform shape and size of biofoam (FIG. 15).

Drying Procedure and Results

Figure 16:
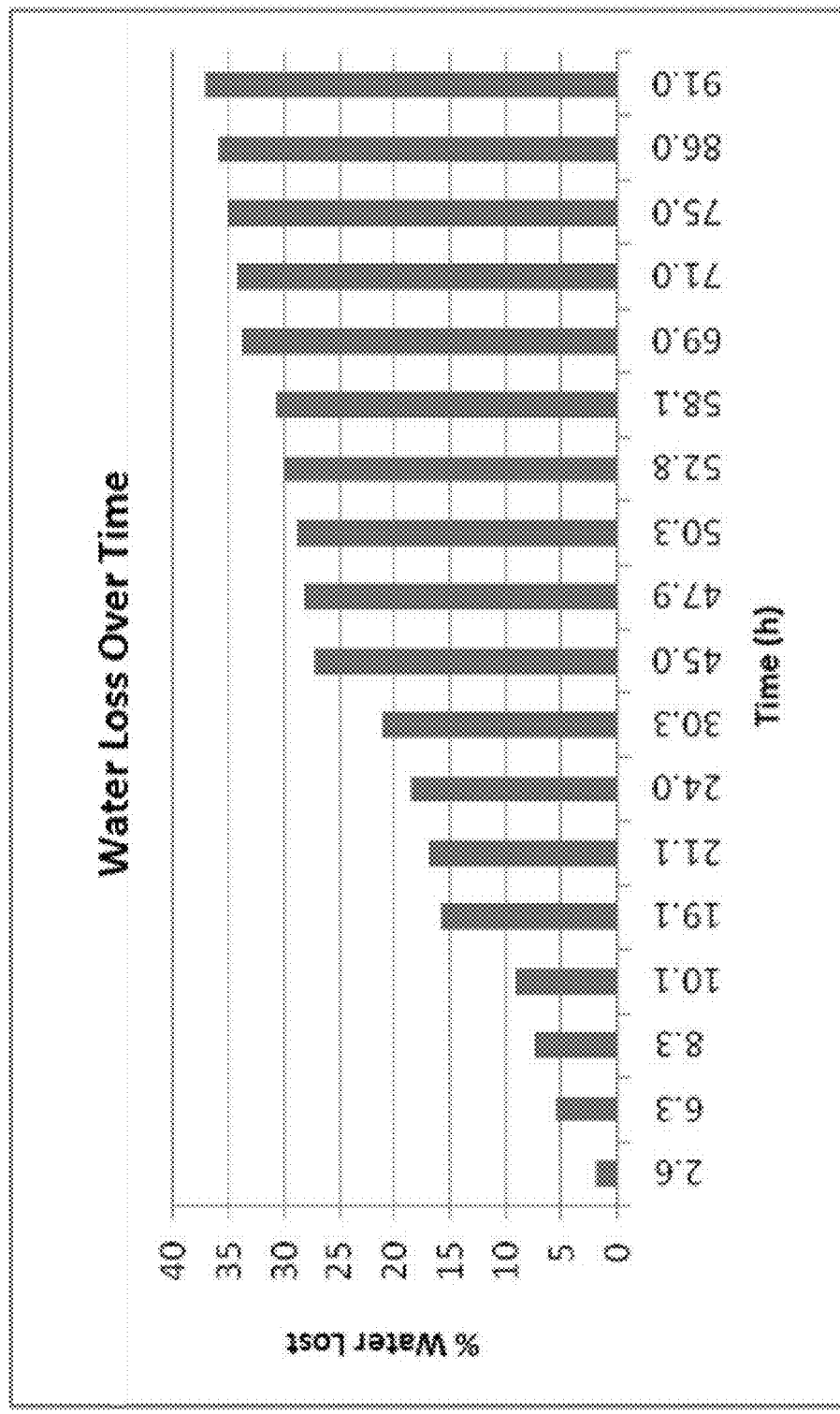
FIG. 16 shows the amount of water lost over time when a biofoam of the present invention is dried in an oven at 50° C. After 72 hours, the weight of the biofoam was stable, indicating excess water had all evaporated.

Prepared biofoams had a water content of approximately 35%, making it necessary to dry the biofoams. Biofoam samples of the preferred formulation (Mixture 55) were placed in ovens at 20° C., 30° C., 40° C., 50° C., 60° C., and 70° C. for 91 hours. The weights of the foam samples were measured prior to drying and were also measured periodically throughout the drying process to determine the amount of water weight lost from the biofoam samples. The best results were achieved at 50° C., where the biofoam samples remained stable in weight after approximately 72 hours (FIG. 16).

Discoloration Tests

Figure 17:
FIG. 17 shows different biofoams undergoing discoloration testing via submersion in coffee.
Figure 18:
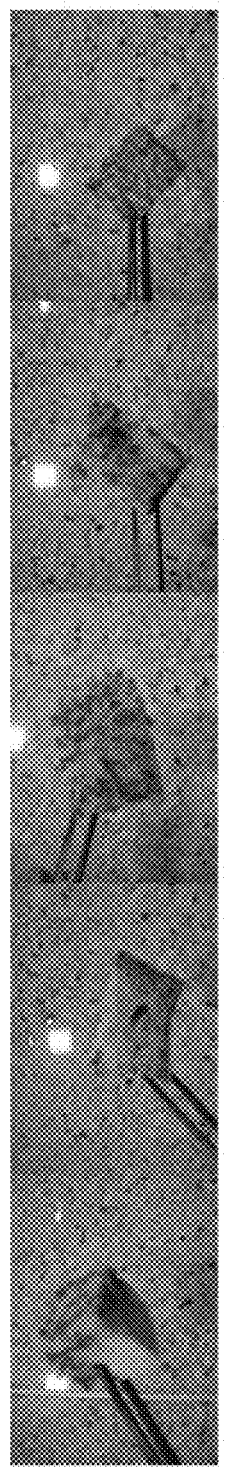
FIG. 18 shows biofoams of the present invention after removal from coffee.

Resistance of the biofoams to discoloration was tested by submersing the biofoams in different concentrations of coffee for 24 hours. Biofoam samples of the preferred formulation (Mixture 55) were placed in solutions of coffee dissolved in distilled water at 0.5 g/l, 1 g/L, 3 g/L, 5 g/L, and 10 g/L (FIG. 17). After 24 hours, the biofoam was rinsed with flowing water for 3 minutes. Discoloration was then qualitatively evaluated, and was highest for the foams exposed to 5 g/L and 10 g/L coffee concentrations (FIG. 18).

Acid Resistance Tests

Figure 19:
FIG. 19 shows different biofoams undergoing acid resistance testing via submersion in (left) 0.1N nitric acid, (center) 0.1N hydrochloric acid, and (right) distilled water.
Figure 20:
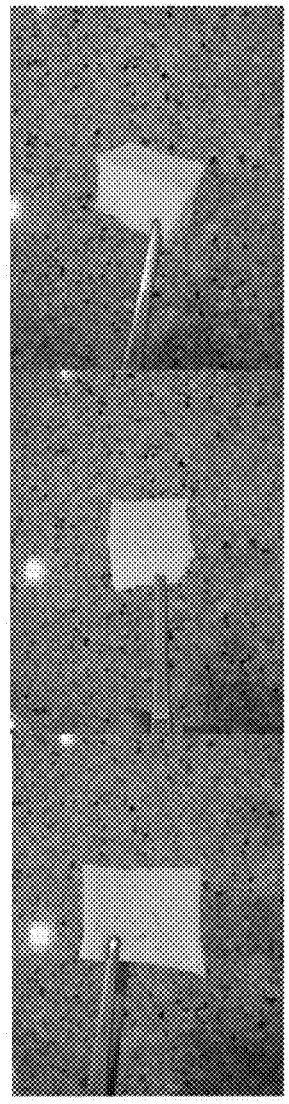
FIG. 20 shows biofoams of the present invention after removal from (a) distilled water, (b) 0.1N hydrochloric acid, and (c) 0.1N nitric acid. Samples pictured were submerged in acid for 24 hours.
Figure 21:
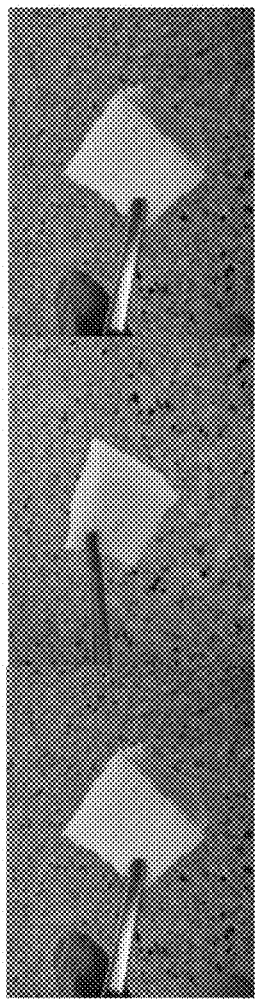
FIG. 21 shows biofoams of the present invention after removal from (a) distilled water, (b) 0.1N hydrochloric acid, and (c) 0.1N nitric acid. Samples pictured were submerged in acid for 48 hours.

Decomposition of the biofoams due to acid exposure was tested. Biofoam samples of the preferred formulation (Mixture 55) were placed in solutions of 0.1N nitric acid, 0.1N hydrochloric acid, or distilled water (control) (FIG. 19) and examined after 24 hours (FIG. 20) and after 48 hours (FIG. 21) of submersion. The biofoams displayed resistance to acid-induced decomposition.

Temperature Resistance Tests

Figure 22:
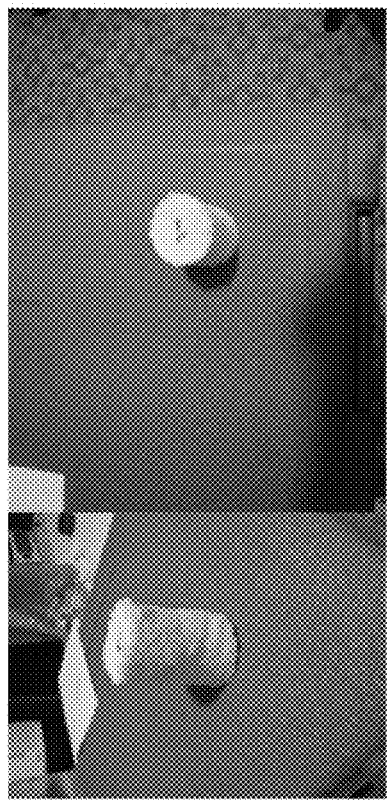
FIG. 22 shows a biofoam of the present invention (a) before and (b) after one hour in a 50° C. oven.

Decomposition of the biofoams under conditions of elevated temperature was tested. Biofoam samples of the preferred formulation (Mixture 55) were placed in ovens at 50° C., 80° C., and/or 120° C., and the internal temperatures of the biofoams were evaluated every 10 minutes. After one hour at 50° C., the biofoam samples did not show any change in color or visible degradation (FIG. 22), although slight decreases in the weights of the samples over time were observed (Table 9).

TABLE 9

Temperature Stability at 50° C.

| Time (minutes) | Weight (g) | Foam Internal Temperature (° C.) |
|---|---|---|
| 0 | 7.00 | 18 |
| 10 | 6.75 | 44.7 |
| 20 | 6.58 | 45.0 |
| 30 | 6.51 | 45.4 |
| 40 | 6.42 | 45.5 |
| 50 | 6.37 | 45.6 |

At 80° C., the biofoam samples exhibited little discoloration or visible degradation (FIG. 23), although slight decreases in the weights of the samples were again observed (Table 10).

TABLE 10

Temperature Stability at 80° C.

| Time (minutes) | Weight (g) | Foam Internal Temperature (° C.) |
|---|---|---|
| 0 | 6.23 | 18 |
| 10 | 5.11 | 62.2 |
| 20 | 5.06 | 68.3 |
| 30 | 5.03 | 72.7 |
| 40 | 5.02 | 75.5 |
| 50 | 5.02 | 76.3 |

At 120° C., the biofoam samples showed visible discoloration and deterioration after only 30 minutes (Table 11, FIG. 24).

TABLE 11

Temperature Stability at 120° C.

| Time (minutes) | Weight (g) | Foam Internal Temperature (° C.) |
|---|---|---|
| 0 | 6.59 | 18 |
| 10 | 5.54 | 81.9 |
| 20 | 5.52 | 113.6 |
| 30 | 5.52 | 115.7 |
| 40 | 5.51 | 116.1 |
| 50 | 5.50 | 116.4 |

Pressure Resistance and Recovery Tests

Figure 25:
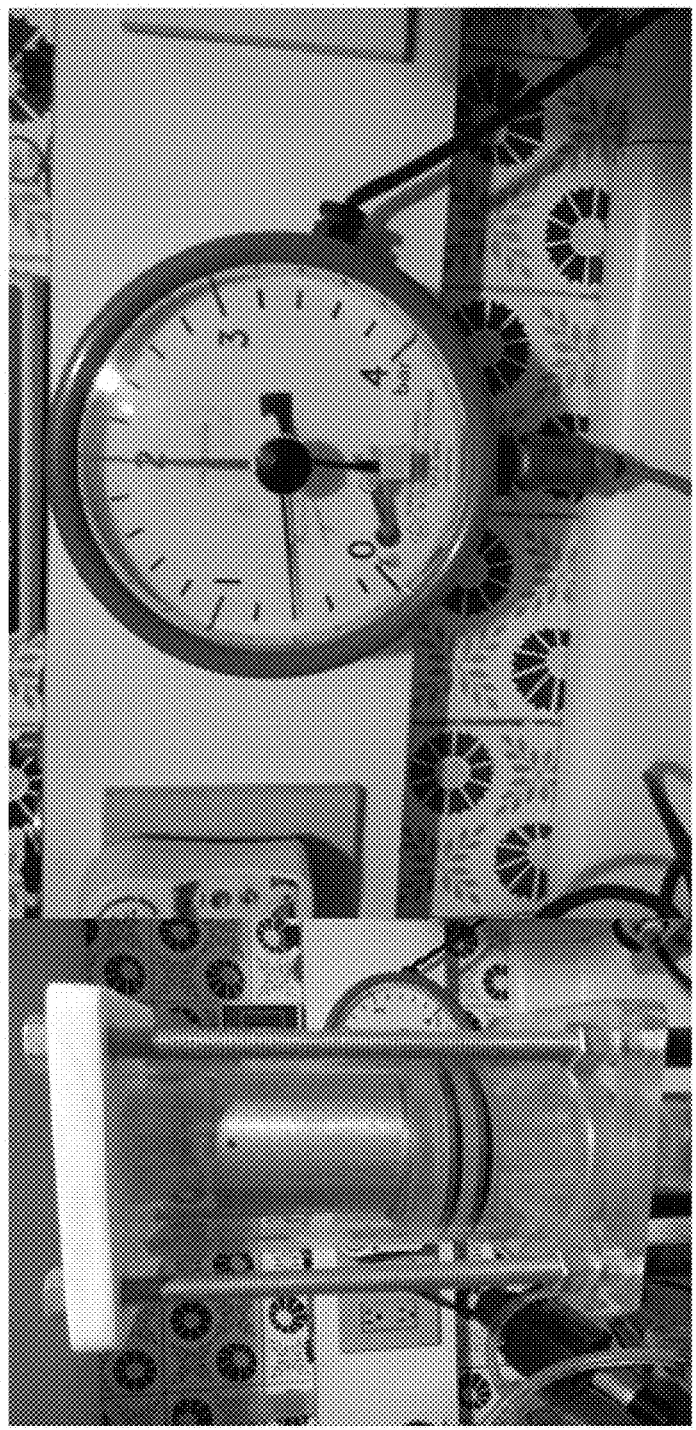
FIG. 25 shows (a) a biofoam of the present invention being subjected to (b) 0.5 bars of pressure.
Figure 26:
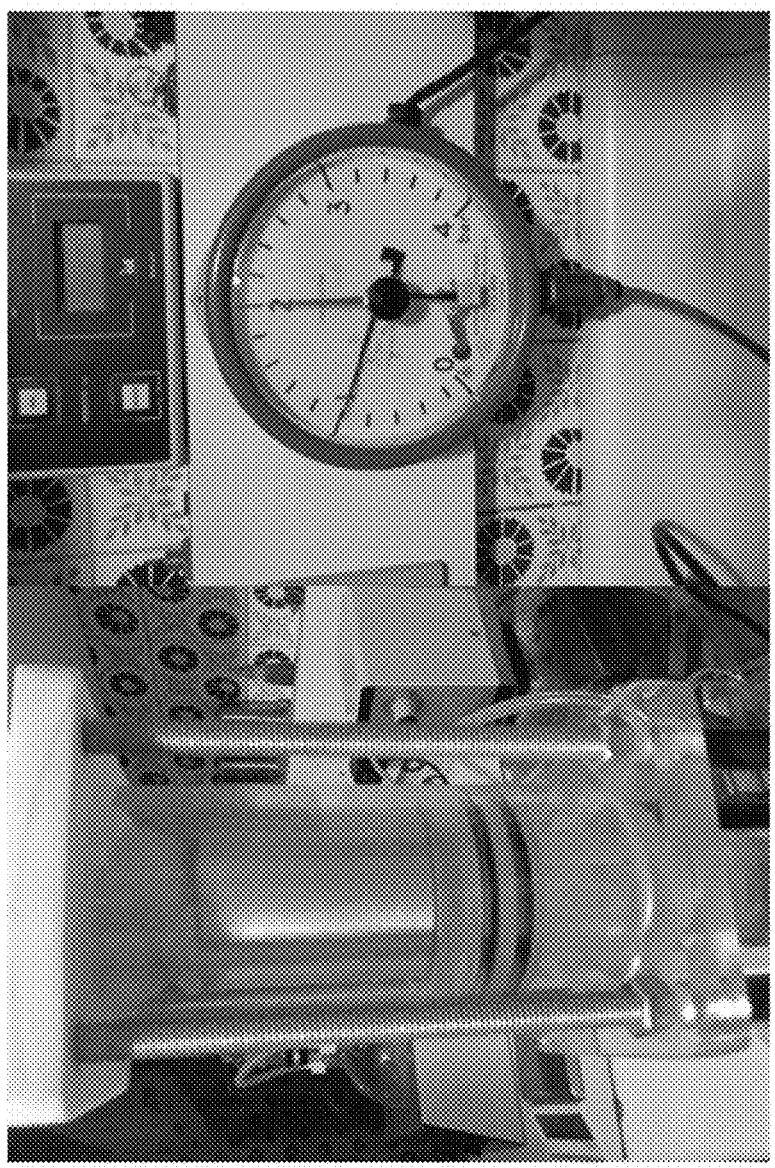
FIG. 26 shows (a) a biofoam of the present invention being subjected to (b) 1 bar of pressure.

The time required for the biofoams to return to their original shapes and/or volumes was assessed. Biofoam samples of the preferred formulation (Mixture 55) were placed in pressure chambers. When 0.5 bars of pressure were applied, recovery time for the foam was approximately 1 second. When 1 bar of pressure was applied, recovery time was approximately 3 seconds (FIGS. 25 and 26).

Mechanical Properties of Biofoam Compositions

Figure 27:
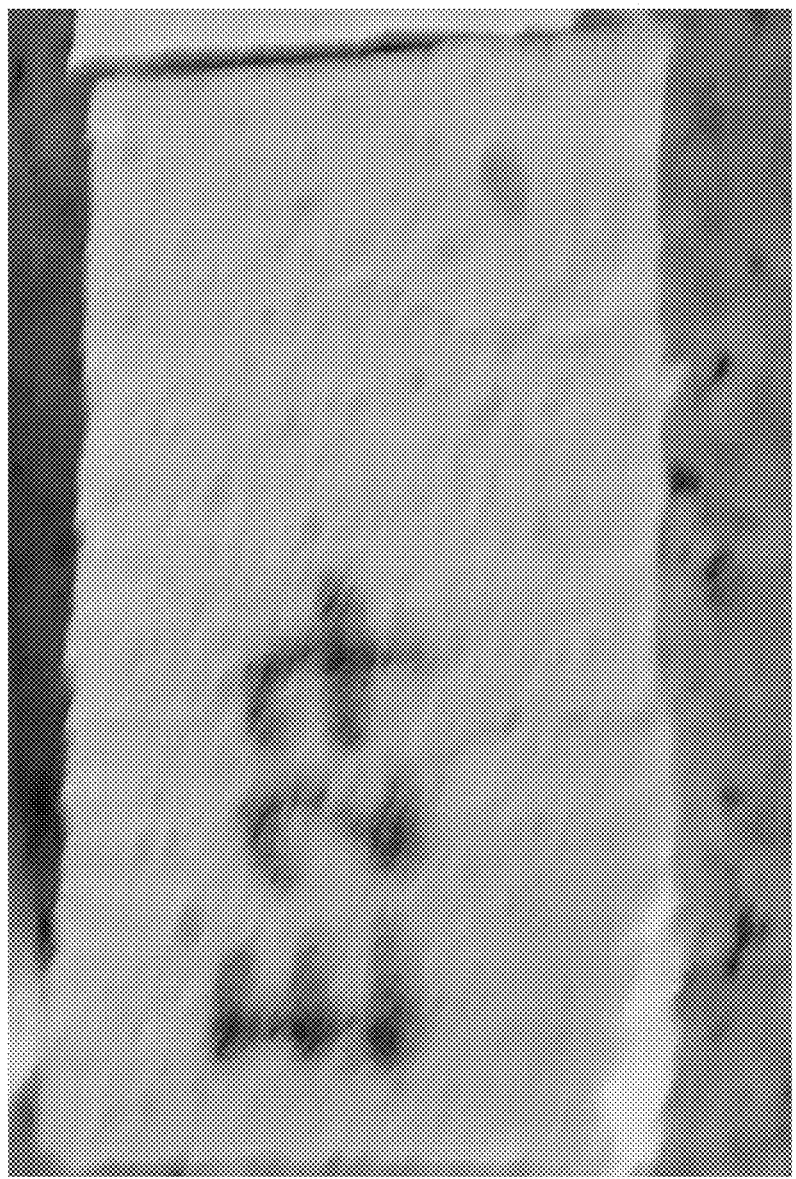
FIG. 27 shows a biofoam of the present invention that displays desirable mechanical properties.

A representative polyurethane biofoam (FIG. 27) was produced from the components listed in Table 12.

TABLE 12

Representative Polyurethane Biofoam

| Component | Amount |
|---|---|
| 4% Chitosan in 0.1N HCl | 50% v/v |
| Polysorbate 80 | 0.35% v/v |
| Microcrystalline cellulose | 2% w/v |
| Bentonite | 0.2% w/v |
| Zeolite | 0.2% w/v |
| Castor Oil | 47.5% v/v |
| Dibutyltin dilaurate | 0.2% v/v |
| DMAE | 1% v/v |
| MDI | 1:5 ratio, MDI:(sum of all other components) |

The cream time for the polyurethane biofoam of Table 12 was 68 seconds; the gel time was 370 seconds. A summary of the mechanical properties of this foam is provided in Table 13.

TABLE 13

Mechanical Properties of a Representative Polyurethane Biofoam

| Drying time | 72 hours |
|---|---|
| Drying temperature | 50° C. |

| Discoloration Resistance Coffee Concentration | Qualitative Results[a] | |
|---|---|---|
| 0.5 g/L | + | |
| 1 g/L | + | |
| 3 g/L | ++ | |
| 5 g/L | ++ | |
| 10 g/L | +++ | |

| | Qualitative Results, | |
|---|---|---|
| Acid Resistance | 24 h | 48 h |
| 0.1N HCl | Resistant | Resistant |
| 0.1N HNO$_3$ | Resistant | Resistant |
| Distilled water (control) | Resistant | Resistant |

| Temperature Resistance | Qualitative Results, 1 h |
|---|---|
| 50° C. | Resistant |
| 80° C. | Resistant |
| 120° C. | Visible Discoloration |

| Pressure Resistance Pressure Applied | Recovery Time |
|---|---|
| 0.5 bar | 1 second |
| 1 bar | 3 seconds |

[a]+ represents weak discoloration,
++ represents medium discoloration, and
+++ represents strong discoloration.

Throughout this application, various publications are referenced. The disclosures of these publications in their entireties are hereby incorporated by reference into this application in order to more fully describe the compounds, compositions, and methods described herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. A polyurethane composition produced by the process comprising
   a. admixing chitosan and a natural oil polyol in a solvent to produce a first admixture, wherein the chitosan is from 60% to 100% acetylated, and the natural oil polyol comprises a hydroxy fatty acid; and
   b. reacting the first admixture with a polyisocyanate to produce the polyurethane composition.

2. The polyurethane composition of claim 1, wherein the chitosan has from 3 to 20 glucosamine units and/or N-acetylglucosamine units.

3. The polyurethane composition of claim 1, wherein the chitosan has from 5 to 10 glucosamine units and/or N-acetylglucosamine units.

4. The polyurethane composition of claim 1, wherein the solvent is water or an aqueous solution of an acid.

5. The polyurethane composition of claim 4, wherein the acid is acetic acid, hydrochloric acid, nitric acid, formic acid, or sulfuric acid.

6. The polyurethane composition of claim 4, wherein the acid is present at a concentration of 0.01 to 1N.

7. The polyurethane composition of claim 1, wherein a surfactant is admixed in step (a), and the surfactant is a polysorbate, a lecithin, or an alcohol ethoxylate.

8. The polyurethane composition of claim 1, wherein the natural oil polyol comprises castor oil, ricinoleic acid, or a combination thereof.

9. The polyurethane composition of claim 1, wherein the polyisocyanate comprises 2,4-toluenediisocyanate alone or in combination with an isomer thereof (TDI), 4,4'-methylene diphenyl diisocyanate (MDI), 4,4'-methylenebis(cyclohexylisocyanate) (H12-MDI), 1-isocyanato-3-isocyanatomethyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethyl-xylylenediisocyanate (TMXDI), or any combination thereof.

10. The polyurethane composition of claim 1, wherein a catalyst is added to the first admixture.

11. The polyurethane composition of claim 10, wherein the catalyst is dimethylethanolamine, triethylenediamine, 3-aminopropyldimethylamine, dimethylcyclohexylamine, propylene glycol, dibutyltin dilaurate, or a combination thereof.

12. The polyurethane composition of claim 1, wherein the first admixture further comprises a clay or clay mineral.

13. The polyurethane composition of claim 12, wherein the clay or clay mineral is a bentonite, a zeolite, or a combination thereof.

14. The polyurethane composition of claim 1, wherein the hydroxy fatty acid comprises a monohydroxy fatty acid, a polyhydroxy fatty acid, or a combination thereof.

15. The polyurethane composition of claim 1, wherein polyurethane further comprises a flame retardant, a color additive, a release agent, a biocide, a blowing agent, or any combination thereof.

16. The polyurethane composition of claim 1, wherein the first admixture further comprises cellulose, guar, or a combination thereof.

17. The polyurethane composition of claim 1, wherein the natural oil polyol comprises castor oil, and the first admixture optionally comprises cellulose, guar, a surfactant, a clay, or any combination thereof.

18. A biofoam comprising the polyurethane composition of claim 1.

19. A molded article comprising the polyurethane composition of claim 1.

* * * * *